US005618722A

United States Patent [19]

Zenno et al.

[11] Patent Number: 5,618,722

[45] Date of Patent: Apr. 8, 1997

[54] PHOTURIS FIREFLY LUCIFERASE GENE

[75] Inventors: Shuhei Zenno; Shinji Shiraishi, both of Yokohamashi; Satoshi Inouye; Kaoru Saigo, both of Tokyo, all of Japan

[73] Assignee: Chisso Corporation, Osaka, Japan

[21] Appl. No.: 231,729

[22] Filed: Apr. 20, 1994

[30] Foreign Application Priority Data

Apr. 21, 1993 [JP] Japan .................................... 5-119050

[51] Int. Cl.$^6$ .............................. C12N 15/53; C12N 9/02

[52] U.S. Cl. ................... 435/252.3; 435/189; 435/320.1; 536/23.2

[58] Field of Search ........................... 536/23.2; 435/189, 435/320.1, 252.3

[56] References Cited

U.S. PATENT DOCUMENTS 5,283,179 2/1994 Wood et al. ................................ 435/8

OTHER PUBLICATIONS

Wienhausen et al., *Photochem Photobiol.*, 42(5):609–612, 1985.

Strause et al., *Insect Biochem.*, 11(4):417–422, 1981.

*Primary Examiner*—Keith D. Hendricks
*Attorney, Agent, or Firm*—Leydig, Voit & Mayer

[57] ABSTRACT

Firefly luciferase gene for making use of the luminescence reaction of luciferase is provided.

11 Claims, 3 Drawing Sheets

FIG. 1

LUC-1, 20mer, 4096 KINDS

T G L P K G V

5′ -ACN, GGN, YTN, CCN, AAR, GGN, GT-3′ (SEQ. ID NO.7)

LUC-2, 20mer, 4096 KINDS

G W L H T/S G D

3′ -CCN, ACC, RAN, GTR, WSN, CCN, CT-5′ (SEQ. ID NO.8)

T : THREONINE
G : GLYCINE
L : LEUCINE
P : PROLINE
K : LYSINE
V : VALINE
W : TRYPTOPHAN
H : HISTIDINE
D : ASPARTIC ACID
T/S : THREONINE OR SERINE

ℓacZ : β-GALCTASE GENE
ℓuc : LUCIFERASE cDNA
Amp$^r$ : AMPICILLIN-RESISTANT GENE
ori : DNA REPLICAT

PHOTURIS FIREFLY LUCIFERASE GENE

This application is the U.S. cognate application of Japanese Application No. 119050/1993 filed Apr. 21, 1993, which is incorporated herein by reference.

BACKGROUND OF THE INVENTION

1. Field of the Invention

This invention relates to a firefly enzyme luciferase gene, a firefly enzyme, a recombinant vector containing the gene and a bacterium containing the recombinant vector.

2. Description of the Related Art

The firefly luciferase catalyzes a reaction forming oxyluciferin, $CO_2$, AMP and pyrophosphoric acid, through D-luciferin as a luminescent substrate, in the presence of ATP, $O_2$ and $Mg^{2+}$. As a result of this reaction, it has been known to emit a light of 560 nm. Luciferase has been used for determining ATP from old time, by utilizing the above ATP-dependent reaction.

de Wet et al isolated luciferase c DNA from *Photinus pyralis* (de Wet, J. R., K. V. Wood, D. R. Helinski and M. Deluca, 1985, *Proc. Natl. Acad. Sci. U.S.A.* 82, 7870–7873). Further, de Wet et al isolated genomic DNA thereof and decided the nucleotide sequence of a gene corresponding to luciferase (de Wet, J. R., K. V. Wood, M. DeLuca, D. R. Helinski and S. Subramani, 1987, *Mol. Cell. Biol.* 7, 725–737).

Masuda et al cloned the luciferase cDNA of *Luciola cruciata* and determined its nucleotide sequence (Masuda, T., H. Tatsumi and E. Nakano, 1989. *Gene* 77, 265–270. Tatsumi et al cloned the luciferase cDNA of *Luciola lateralis* and determined its nucleotide sequence (Tatsumi et al, H., N. Kajiyama and E. Nakano, 1992, *Biochim. Biophys. Acta* 1131 161–165).

Further, Wood et al isolated luciferase cDNAs originated from *Pyrophorus plagiophthalamus* and determined its nucleotide sequence (Wood, K. V., Y. A. Lam, H. H. Seliger and W. D. McElroy, 1989, *Science* 244 700–702).

Recently, utilizing the luminescence reaction of luciferase, measurement of the number of bacterial cells, immunoassay and development of clinical inspection chemicals according to DNA probe method have been attempted. The luciferin·luciferase reaction can be measured and detected simply, rapidly and with a good sensitivity by means of a luminescence-measuring instrument. Further, using the luciferase gene as a reporter, the quantity of gene expressed and the site of gene expressed have come to be examined.

(Problem to be Solved by the Invention)

As described above, firefly luciferase is a very important enzyme as a reporter protein, and application to various measurement systems of bioluminescent systems have now been desired and expected due to the high level of its detection sensitivity. As a first step therefor, it is indispensable to obtain luciferase gene and protein. Isolation of luciferase gene directed to Photuris firefly and its expression by means of *Escherichia coli* have not yet been reported.

The present inventors have made extensive research, and as a result, have succeeded in isolating luciferase gene from Nothem American firefly (Photuris) and elucidating its primary structure, and further have succeeded in producing *Escherichia coli* expressing the gene in a large quantity; thus we have completed the present invention.

SUMMARY OF THE INVENTION

As apparent from the foregoing, the object of the present invention is, in view of the above technical situation, to provide luciferase gene of Northern American firefly (Photuris) and enzyme, and further to provide a recombinant vector containing the gene and a bacterium containing the recombinant vector.

The present invention has the following constitutions (1) to (8):

(1) A firefly enzyme luciferase gene comprising a nucleotide sequence expressed by the following:

| | | | | | | | | | | | | | | | | |
|---|---|---|---|---|---|---|---|---|---|---|---|---|---|---|---|---|
| ATG | TCN | ATH | GAR | AAY | AAY | ATH | YTN | ATH | GGN | CCN | CCN | CCN | TAY | TAY | CCN | 48 |
| Met | Ser | Ile | Glu | Asn | Asn | Ile | Leu | Ile | Gly | Pro | Pro | Pro | Tyr | Tyr | Pro | |
| 1 | | | | 5 | | | | | 10 | | | | | 15 | | |
| YTN | GAR | GAR | GGN | ACN | GCN | GGN | GAR | CAR | YTN | CAY | MGN | GCN | ATH | TCN | MGN | 96 |
| Leu | Glu | Glu | Gly | Thr | Ala | Gly | Glu | Gln | Leu | His | Xaa | Ala | Ile | Ser | Xaa | |
| | | | 20 | | | | | 25 | | | | | 30 | | | |
| TAY | GCN | GCN | GTN | CCN | GGN | ACN | YTN | GCN | TAY | ACN | GAY | GTN | CAY | ACN | GAR | 144 |
| Tyr | Ala | Ala | Val | Pro | Gly | Thr | Leu | Ala | Tyr | Thr | Asp | Val | His | Thr | Glu | |
| | | 35 | | | | | 40 | | | | | 45 | | | | |
| YTN | GAR | GTN | ACN | TAY | AAR | GAR | TTY | YTN | GAY | GTN | ACN | TGY | CGC | YTN | GCN | 192 |
| Leu | Glu | Val | Thr | Tyr | Lys | Glu | Phe | Leu | Asp | Val | Thr | Cys | Arg | Leu | Ala | |
| | 50 | | | | | 55 | | | | | 60 | | | | | |
| GAR | GCN | ATG | AAR | AAY | TAY | GGN | YTN | GGN | YTN | CAR | CAY | ACN | ATH | TCN | GTN | 240 |
| Glu | Ala | Met | Lys | Asn | Tyr | Gly | Leu | Gly | Leu | Gln | His | Thr | Ile | Ser | Val | |
| 65 | | | | | 70 | | | | | 75 | | | | | 80 | |
| TGY | TCN | GAR | AAY | TGY | GTN | CAR | TTY | TTY | ATG | CCN | ATH | TGY | GCN | GCN | YTN | 288 |
| Cys | Ser | Glu | Asn | Cys | Val | Gln | Phe | Phe | Met | Pro | Ile | Cys | Ala | Ala | Leu | |
| | | | | 85 | | | | | 90 | | | | | 95 | | |
| TAY | GTN | GGN | GTN | GCN | ACN | GCN | CCN | ACN | AAY | GAY | ATH | TAY | AAY | GAR | MGN | 336 |
| Tyr | Val | Gly | Val | Ala | Thr | Ala | Pro | Thr | Asn | Asp | Ile | Tyr | Asn | Glu | Xaa | |
| | | | 100 | | | | | 105 | | | | | 110 | | | |
| GAR | YTN | TAY | AAY | TCN | YTN | TCN | ATH | TCN | CAR | CCN | ACN | GTN | GTN | TTY | ACN | 384 |
| Glu | Leu | Tyr | Asn | Ser | Leu | Ser | Ile | Ser | Gln | Pro | Thr | Val | Val | Phe | Thr | |
| | | 115 | | | | | 120 | | | | | 125 | | | | |

-continued

| | | | | | | | | | | | | | | | | |
|---|---|---|---|---|---|---|---|---|---|---|---|---|---|---|---|---|
| TCN | MGN | AAY | TCN | YTN | CAR | AAR | ATH | YTN | GGN | GTN | CAR | TCN | MGN | YTN | CCN | 432 |
| Ser | Xaa | Asn | Ser | Leu | Gln | Lys | Ile | Leu | Gly | Val | Gln | Ser | Xaa | Leu | Pro | |
| | 130 | | | | | 135 | | | | | 140 | | | | | |
| ATH | ATH | AAR | AAR | ATH | ATH | ATH | YTN | GAY | GGN | AAR | AAR | GAY | TAY | YTN | GGN | 480 |
| Ile | Ile | Lys | Lys | Ile | Ile | Ile | Leu | Asp | Gly | Lys | Lys | Asp | Tyr | Leu | Gly | |
| 145 | | | | | 150 | | | | | 155 | | | | | 160 | |
| TAY | CAR | TCN | ATG | CAR | TCN | TTY | ATG | AAR | GAR | CAY | GTN | CCN | GCN | AAY | TTY | 528 |
| Tyr | Gln | Ser | Met | Gln | Ser | Phe | Met | Lys | Glu | His | Val | Pro | Ala | Asn | Phe | |
| | | | | 165 | | | | | 170 | | | | | 175 | | |
| AAY | GTN | TCN | GCN | TTY | AAR | CCN | YTN | TCN | TTY | GAY | YTN | GAY | MGN | GTN | GCN | 576 |
| Asn | Val | Ser | Ala | Phe | Lys | Pro | Leu | Ser | Phe | Asp | Leu | Asp | Xaa | Val | Ala | |
| | | | 180 | | | | | 185 | | | | | 190 | | | |
| TGY | ATH | ATG | AAY | TCN | TCN | GGN | TCN | ACN | GGN | YTN | CCN | AAR | GGN | GTN | CCN | 624 |
| Cys | Ile | Met | Asn | Ser | Ser | Gly | Ser | Thr | Gly | Leu | Pro | Lys | Gly | Val | Pro | |
| | | 195 | | | | | 200 | | | | | 205 | | | | |
| ATH | TCN | CAY | MGN | AAY | ACN | ATH | TAY | MGN | TTY | TCN | CAY | TGY | MGN | GAY | CCN | 672 |
| Ile | Ser | His | Xaa | Asn | Thr | Ile | Tyr | Xaa | Phe | Ser | His | Cys | Xaa | Asp | Pro | |
| | 210 | | | | | 215 | | | | | 220 | | | | | |
| GTN | TTY | GGN | AAY | CAR | ATH | ATH | CCN | GAY | ACN | ACN | ATH | YTN | TGY | GCN | GTN | 720 |
| Val | Phe | Gly | Asn | Gln | Ile | Ile | Pro | Asp | Thr | Thr | Ile | Leu | Cys | Ala | Val | |
| 225 | | | | | 230 | | | | | 235 | | | | | 240 | |
| CCN | TTY | CAY | CAY | GCN | TTY | GGN | ACN | TTY | ACN | AAY | YTN | GGN | TAY | YTN | ATH | 768 |
| Pro | Phe | His | His | Ala | Phe | Gly | Thr | Phe | Thr | Asn | Leu | Gly | Tyr | Leu | Ile | |
| | | | | 245 | | | | | 250 | | | | | 255 | | |
| TGY | GGN | TTY | CAY | GTN | GTN | YTN | ATG | TAY | MGN | TTY | AAY | GAR | CAY | YTN | TTY | 816 |
| Cys | Gly | Phe | His | Val | Val | Leu | Met | Tyr | Xaa | Phe | Asn | Glu | His | Leu | Phe | |
| | | | 260 | | | | | 265 | | | | | 270 | | | |
| YTN | CAR | ACN | YTN | CAR | GAY | TAY | AAR | TGY | CAR | TCN | GCN | YTN | YTN | GTN | CCN | 864 |
| Leu | Gln | Thr | Leu | Gln | Asp | Tyr | Lys | Cys | Gln | Ser | Ala | Leu | Leu | Val | Pro | |
| | | 275 | | | | | 280 | | | | | 285 | | | | |
| ACN | GTN | YTN | GCN | TTY | YTN | GCN | AAR | AAY | CCN | YTN | GTN | GAY | AAR | TAY | GAY | 912 |
| Thr | Val | Leu | Ala | Phe | Leu | Ala | Lys | Asn | Pro | Leu | Val | Asp | Lys | Tyr | Asp | |
| | 290 | | | | | 295 | | | | | 300 | | | | | |
| YTN | TCN | AAY | YTN | CAY | GAR | ATH | GCN | TCN | GGN | GGN | GCN | CCN | YTN | TCN | AAR | 960 |
| Leu | Ser | Asn | Leu | His | Glu | Ile | Ala | Ser | Gly | Gly | Ala | Pro | Leu | Ser | Lys | |
| 305 | | | | | 310 | | | | | 315 | | | | | 320 | |
| GAR | ATH | TCN | GAR | ATH | GCN | GCN | AAR | MGN | TTY | AAR | YTN | CCN | GGN | ATH | MGN | 1008 |
| Glu | Ile | Ser | Glu | Ile | Ala | Ala | Lys | Xaa | Phe | Lys | Leu | Pro | Gly | Ile | Xaa | |
| | | | | 325 | | | | | 330 | | | | | 335 | | |
| CAR | GGN | TAY | GGN | YTN | ACN | GAR | ACN | ACN | TGY | GCN | ATH | GTN | ATH | ACN | GCN | 1056 |
| Gln | Gly | Tyr | Gly | Leu | Thr | Glu | Thr | Thr | Cys | Ala | Ile | Val | Ile | Thr | Ala | |
| | | | 340 | | | | | 345 | | | | | 350 | | | |
| GAR | GGN | GAR | TTY | AAR | YTN | GGN | GCN | GTN | GGN | AAR | GTN | GTN | CCN | TTY | TAY | 1104 |
| Glu | Gly | Glu | Phe | Lys | Leu | Gly | Ala | Val | Gly | Lys | Val | Val | Pro | Phe | Tyr | |
| | | 355 | | | | | 360 | | | | | 365 | | | | |
| TCN | YTN | AAR | GTN | YTN | GAY | YTN | AAY | ACN | GGN | AAR | AAR | YTN | GGN | CCN | AAY | 1152 |
| Ser | Leu | Lys | Val | Leu | Asp | Leu | Asn | Thr | Gly | Lys | Lys | Leu | Gly | Pro | Asn | |
| | 370 | | | | | 375 | | | | | 380 | | | | | |
| GAR | MGN | GGN | GAR | ATH | TGY | TTY | AAR | GGN | CCN | ATG | ATH | ATG | AAR | GGN | TAY | 1200 |
| Glu | Xaa | Gly | Glu | Ile | Cys | Phe | Lys | Gly | Pro | Met | Ile | Met | Lys | Gly | Tyr | |
| 385 | | | | | 390 | | | | | 395 | | | | | 400 | |
| ATH | AAY | AAY | CCN | GAR | GCN | ACN | CGC | GAN | YTN | ATH | GAY | GAR | GAR | GGN | TGG | 1248 |
| Ile | Asn | Asn | Pro | Glu | Ala | Thr | Arg | Xaa | Leu | Ile | Asp | Glu | Glu | Gly | Trp | |
| | | | | 405 | | | | | 410 | | | | | 415 | | |
| ATH | CAY | TCN | GGN | GAY | ATH | GGN | TAY | TTY | GAY | GAR | GAY | GGN | CAY | GTN | TAY | 1296 |
| Ile | His | Ser | Gly | Asp | Ile | Gly | Tyr | Phe | Asp | Glu | Asp | Gly | His | Val | Tyr | |
| | | | 420 | | | | | 425 | | | | | 430 | | | |
| ATH | GTN | GAY | MGN | YTN | AAR | TCN | YTN | ATH | AAR | TAY | AAR | GGN | TAY | CAR | GTN | 1344 |
| Ile | Val | Asp | Xaa | Leu | Lys | Ser | Leu | Ile | Lys | Tyr | Lys | Gly | Tyr | Gln | Val | |
| | | 435 | | | | | 440 | | | | | 445 | | | | |
| CCN | CCN | GCN | GAR | YTN | GAR | GCN | YTN | YTN | YTN | CAR | CAY | CCN | TTY | ATH | GAR | 1392 |
| Pro | Pro | Ala | Glu | Leu | Glu | Ala | Leu | Leu | Leu | Gln | His | Pro | Phe | Ile | Glu | |
| | 450 | | | | | 455 | | | | | 460 | | | | | |

-continued

| | | | | | | | | | | | | | | | | |
|---|---|---|---|---|---|---|---|---|---|---|---|---|---|---|---|---|
| GAY | GCN | GGN | GTN | GCN | GGN | GTN | CCN | GAY | GAR | GTN | GCN | GGN | GAY | YTN | CCN | 1440 |
| Asp | Ala | Gly | Val | Ala | Gly | Val | Pro | Asp | Glu | Val | Ala | Gly | Asp | Leu | Pro | |
| 465 | | | | | 470 | | | | | 475 | | | | | 480 | |
| GGN | GCN | GTN | GTN | GTN | YTN | AAR | GAR | GGN | AAR | TCN | ATH | ACN | GAR | AAR | GAR | 1488 |
| Gly | Ala | Val | Val | Val | Leu | Lys | Glu | Gly | Lys | Ser | Ile | Thr | Glu | Lys | Glu | |
| | | | | 485 | | | | | 490 | | | | | 495 | | |
| ATH | CAR | GAY | TAY | GTN | GCN | GGN | CAR | GTN | ACN | TCN | TCN | AAR | AAR | YTN | MGN | 1536 |
| Ile | Gln | Asp | Tyr | Val | Ala | Gly | Gln | Val | Thr | Ser | Ser | Lys | Lys | Leu | Xaa | |
| | | | 500 | | | | | 505 | | | | | 510 | | | |
| GGN | GGN | GTN | GAR | TTY | GTN | AAR | GAR | GTN | CCN | AAR | GGN | TTY | ACN | GGN | AAR | 1584 |
| Gly | Gly | Val | Glu | Phe | Val | Lys | Glu | Val | Pro | Lys | Gly | Phe | Thr | Gly | Lys | |
| | | 515 | | | | | 520 | | | | | 525 | | | | |
| ATH | GAY | ACN | MGN | AAR | ATH | AAR | GAR | ATH | YTN | ATH | AAR | GCN | CAR | AAR | GGN | 1632 |
| Ile | Asp | Thr | Xaa | Lys | Ile | Lys | Glu | Ile | Leu | Ile | Lys | Ala | Gln | Lys | Gly | |
| | 530 | | | | | 535 | | | | | 540 | | | | | |
| AAR | TCN | AAR | TCN | AAR | GCN | AAR | YTN | TRR | | | | | | | | 1659 |
| Lys | Ser | Lys | Ser | Lys | Ala | Lys | Leu | | | | | | | | | |
| 545 | | | | | 550 | | | | | | | | | | | |

(SEQ ID NO:1), wherein the sequence is displayed in numbered triplets of capital letters, which numbers proceed sequentially from left to right and from the 5' terminus to the 3' terminus; and the sequence of capital letters represent the purine and pyrimidine bases of the nucleotide sequence, as follows:

A is adenine; G is guanine; C is cytosine; T is thymine; R is A or G; Y is T or C; N is A, T, C, or G; H is A, C, or T; and M is A or C;

wherein further:

(a) triplet number 553 thereof is TAA or TAG or TGA;

(b) for triplets numbered 8, 17, 26, 40, 49, 57, 63, 72, 74, 96, 114, 118, 133, 137, 143, 152, 159, 184, 189, 203, 237, 252, 255, 263, 271, 273, 276, 286, 287, 291, 294, 299, 305, 308, 318, 332, 341, 358, 373, 375, 381, 410, 437, 440, 453, 456, 457, 458, 479, 486, 511, 538, and 552, if the 3' nucleotide of a triplet is A or G, then the 5' nucleotide of said triplet is T or C, or if the 3' nucleotide of a triplet is T or C, then the 5' nucleotide of said triplet is C; and if the 5' nucleotide of a triplet is C, then the 3' nucleotide of said triplet is A, T, C, or G, or if the 5' nucleotide of a triplet is T, then the 3' nucleotide of said triplet is A or G; and (c) for triplets numbered 28, 32, 112, 130, 142, 190, 212, 217, 222, 266, 329, 336, 386, 436, 512, and 532, if the 3' nucleotide of a triplet is T or C, then the 5' nucleotide of said triplet is A or C, or if the 3' nucleotide of a triplet is T or C, then the 5' nucleotide of said triplet is C; and if the 5' nucleotide of a triplet is G, then the 3' nucleotide of said triplet is A, T, C, or G, or if the 5' nucleotide of a triplet is A, then the 3' nucleotide of said triplet is A or G; Preferably a firefly enzyme luciferase gene comprises a nucleotide sequence expressed by the following:

| | | | | | | | | | | | | | | | | |
|---|---|---|---|---|---|---|---|---|---|---|---|---|---|---|---|---|
| ATG | TCN | ATH | GAR | AAY | AAY | ATH | YTN | ATH | GGN | CCN | CCN | CCN | TAY | TAY | CCN | 48 |
| Met | Ser | Ile | Glu | Asn | Asn | Ile | Leu | Ile | Gly | Pro | Pro | Pro | Tyr | Tyr | Pro | |
| 1 | | | | 5 | | | | | 10 | | | | | 15 | | |
| YTN | GAR | GAR | GGN | ACN | GCN | GGN | GAR | CAR | YTN | CAY | MGN | GCN | ATH | TCN | MGN | 96 |
| Leu | Glu | Glu | Gly | Thr | Ala | Gly | Glu | Gln | Leu | His | Arg | Ala | Ile | Ser | Arg | |
| | | | 20 | | | | | 25 | | | | | 30 | | | |
| TAY | GCN | GCN | GTN | CCN | GGN | ACN | YTN | GCN | TAY | ACN | GAY | GTN | CAY | ACN | GAR | 144 |
| Tyr | Ala | Ala | Val | Pro | Gly | Thr | Leu | Ala | Tyr | Thr | Asp | Val | His | Thr | Glu | |
| | | 35 | | | | | 40 | | | | | 45 | | | | |
| YTN | GAR | GTN | ACN | TAY | AAR | GAR | TTY | YTN | GAY | GTN | ACN | TGY | CGC | YTN | GCN | 192 |
| Leu | Glu | Val | Thr | Tyr | Lys | Glu | Phe | Leu | Asp | Val | Thr | Cys | Arg | Leu | Ala | |
| | 50 | | | | | 55 | | | | | 60 | | | | | |
| GAR | GCN | ATG | AAR | AAY | TAY | GGN | YTN | GGN | YTN | CAR | CAY | ACN | ATH | TCN | GTN | 240 |
| Glu | Ala | Met | Lys | Asn | Tyr | Gly | Leu | Gly | Leu | Gln | His | Thr | Ile | Ser | Val | |
| 65 | | | | | 70 | | | | | 75 | | | | | 80 | |
| TGY | TCN | GAR | AAY | TGY | GTN | CAR | TTY | TTY | ATG | CCN | ATH | TGY | GCN | GCN | YTN | 288 |
| Cys | Ser | Glu | Asn | Cys | Val | Gln | Phe | Phe | Met | Pro | Ile | Cys | Ala | Ala | Leu | |
| | | | | 85 | | | | | 90 | | | | | 95 | | |
| TAY | GTN | GGN | GTN | GCN | ACN | GCN | CCN | ACN | AAY | GAY | ATH | TAY | AAY | GAR | MGN | 336 |
| Tyr | Val | Gly | Val | Ala | Thr | Ala | Pro | Thr | Asn | Asp | Ile | Tyr | Asn | Glu | Arg | |
| | | | 100 | | | | | 105 | | | | | 110 | | | |
| GAR | YTN | TAY | AAY | TCN | YTN | TCN | ATH | TCN | CAR | CCN | ACN | GTN | GTN | TTY | ACN | 384 |
| Glu | Leu | Tyr | Asn | Ser | Leu | Ser | Ile | Ser | Gln | Pro | Thr | Val | Val | Phe | Thr | |
| | | 115 | | | | | 120 | | | | | 125 | | | | |

-continued

```
TCN  MGN  AAY  TCN  YTN  CAR  AAR  ATH  YTN  GGN  GTN  CAR  TCN  MGN  YTN  CCN   432
Ser  Arg  Asn  Ser  Leu  Gln  Lys  Ile  Leu  Gly  Val  Gln  Ser  Arg  Leu  Pro
     130                      135                      140

ATH  ATH  AAR  AAR  ATH  ATH  ATH  YTN  GAY  GGN  AAR  AAR  GAY  TAY  YTN  GGN   480
Ile  Ile  Lys  Lys  Ile  Ile  Ile  Leu  Asp  Gly  Lys  Lys  Asp  Tyr  Leu  Gly
145                      150                      155                      160

TAY  CAR  TCN  ATG  CAR  TCN  TTY  ATG  AAR  GAR  CAY  GTN  CCN  GCN  AAY  TTY   528
Tyr  Gln  Ser  Met  Gln  Ser  Phe  Met  Lys  Glu  His  Val  Pro  Ala  Asn  Phe
                    165                      170                      175

AAY  GTN  TCN  GCN  TTY  AAR  CCN  YTN  TCN  TTY  GAY  YTN  GAY  MGN  GTN  GCN   576
Asn  Val  Ser  Ala  Phe  Lys  Pro  Leu  Ser  Phe  Asp  Leu  Asp  Arg  Val  Ala
               180                      185                      190

TGY  ATH  ATG  AAY  TCN  TCN  GGN  TCN  ACN  GGN  YTN  CCN  AAR  GGN  GTN  CCN   624
Cys  Ile  Met  Asn  Ser  Ser  Gly  Ser  Thr  Gly  Leu  Pro  Lys  Gly  Val  Pro
          195                      200                      205

ATH  TCN  CAY  MGN  AAY  ACN  ATH  TAY  MGN  TTY  TCN  CAY  TGY  MGN  GAY  CCN   672
Ile  Ser  His  Arg  Asn  Thr  Ile  Tyr  Arg  Phe  Ser  His  Cys  Arg  Asp  Pro
     210                      215                      220

GTN  TTY  GGN  AAY  CAR  ATH  ATH  CCN  GAY  ACN  ACN  ATH  YTN  TGY  GCN  GTN   720
Val  Phe  Gly  Asn  Gln  Ile  Ile  Pro  Asp  Thr  Thr  Ile  Leu  Cys  Ala  Val
225                      230                      235                      240

CCN  TTY  CAY  CAY  GCN  TTY  GGN  ACN  TTY  ACN  AAY  YTN  GGN  TAY  YTN  ATH   768
Pro  Phe  His  His  Ala  Phe  Gly  Thr  Phe  Thr  Asn  Leu  Gly  Tyr  Leu  Ile
                    245                      250                      255

TGY  GGN  TTY  CAY  GTN  GTN  YTN  ATG  TAY  MGN  TTY  AAY  GAR  CAY  YTN  TTY   816
Cys  Gly  Phe  His  Val  Val  Leu  Met  Tyr  Arg  Phe  Asn  Glu  His  Leu  Phe
               260                      265                      270

YTN  CAR  ACN  YTN  CAR  GAY  TAY  AAR  TGY  CAR  TCN  GCN  YTN  YTN  GTN  CCN   864
Leu  Gln  Thr  Leu  Gln  Asp  Tyr  Lys  Cys  Gln  Ser  Ala  Leu  Leu  Val  Pro
          275                      280                      285

ACN  GTN  YTN  GCN  TTY  YTN  GCN  AAR  AAY  CCN  YTN  GTN  GAY  AAR  TAY  GAY   912
Thr  Val  Leu  Ala  Phe  Leu  Ala  Lys  Asn  Pro  Leu  Val  Asp  Lys  Tyr  Asp
     290                      295                      300

YTN  TCN  AAY  YTN  CAY  GAR  ATH  GCN  TCN  GGN  GGN  GCN  CCN  YTN  TCN  AAR   960
Leu  Ser  Asn  Leu  His  Glu  Ile  Ala  Ser  Gly  Gly  Ala  Pro  Leu  Ser  Lys
305                      310                      315                      320

GAR  ATH  TCN  GAR  ATH  GCN  GCN  AAR  MGN  TTY  AAR  YTN  CCN  GGN  ATH  MGN  1008
Glu  Ile  Ser  Glu  Ile  Ala  Ala  Lys  Arg  Phe  Lys  Leu  Pro  Gly  Ile  Arg
                    325                      330                      335

CAR  GGN  TAY  GGN  YTN  ACN  GAR  ACN  ACN  TGY  GCN  ATH  GTN  ATH  ACN  GCN  1056
Gln  Gly  Tyr  Gly  Leu  Thr  Glu  Thr  Thr  Cys  Ala  Ile  Val  Ile  Thr  Ala
               340                      345                      350

GAR  GGN  GAR  TTY  AAR  YTN  GGN  GCN  GTN  GGN  AAR  GTN  GTN  CCN  TTY  TAY  1104
Glu  Gly  Glu  Phe  Lys  Leu  Gly  Ala  Val  Gly  Lys  Val  Val  Pro  Phe  Tyr
          355                      360                      365

TCN  YTN  AAR  GTN  YTN  GAY  YTN  AAY  ACN  GGN  AAR  AAR  YTN  GGN  CCN  AAY  1152
Ser  Leu  Lys  Val  Leu  Asp  Leu  Asn  Thr  Gly  Lys  Lys  Leu  Gly  Pro  Asn
     370                      375                      380

GAR  MGN  GGN  GAR  ATH  TGY  TTY  AAR  GGN  CCN  ATG  ATH  ATG  AAR  GGN  TAY  1200
Glu  Arg  Gly  Glu  Ile  Cys  Phe  Lys  Gly  Pro  Met  Ile  Met  Lys  Gly  Tyr
385                      390                      395                      400

ATH  AAY  AAY  CCN  GAR  GCN  ACN  CGC  GAR  YTN  ATH  GAY  GAR  GAR  GGN  TGG  1248
Ile  Asn  Asn  Pro  Glu  Ala  Thr  Arg  Glu  Leu  Ile  Asp  Glu  Glu  Gly  Trp
                    405                      410                      415

ATH  CAY  TCN  GGN  GAY  ATH  GGN  TAY  TTY  GAY  GAR  GAY  GGN  CAY  GTN  TAY  1296
Ile  His  Ser  Gly  Asp  Ile  Gly  Tyr  Phe  Asp  Glu  Asp  Gly  His  Val  Tyr
               420                      425                      430

ATH  GTN  GAY  MGN  YTN  AAR  TCN  YTN  ATH  AAR  TAY  AAR  GGN  TAY  CAR  GTN  1344
Ile  Val  Asp  Arg  Leu  Lys  Ser  Leu  Ile  Lys  Tyr  Lys  Gly  Tyr  Gln  Val
          435                      440                      445

CCN  CCN  GCN  GAR  YTN  GAR  GCN  YTN  YTN  YTN  CAR  CAY  CCN  TTY  ATH  GAR  1392
Pro  Pro  Ala  Glu  Leu  Glu  Ala  Leu  Leu  Leu  Gln  His  Pro  Phe  Ile  Glu
     450                      455                      460
```

-continued

| | | | | | | | | | | | | | | | | |
|---|---|---|---|---|---|---|---|---|---|---|---|---|---|---|---|---|
| GAY | GCN | GGN | GTN | GCN | GGN | GTN | CCN | GAY | GAR | GTN | GCN | GGN | GAY | YTN | CCN | 1440 |
| Asp | Ala | Gly | Val | Ala | Gly | Val | Pro | Asp | Glu | Val | Ala | Gly | Asp | Leu | Pro | |
| 465 | | | | | 470 | | | | | 475 | | | | | 480 | |
| GGN | GCN | GTN | GTN | GTN | YTN | AAR | GAR | GGN | AAR | TCN | ATH | ACN | GAR | AAR | GAR | 1488 |
| Gly | Ala | Val | Val | Val | Leu | Lys | Glu | Gly | Lys | Ser | Ile | Thr | Glu | Lys | Glu | |
| | | | | 485 | | | | | 490 | | | | | 495 | | |
| ATH | CAR | GAY | TAY | GTN | GCN | GGN | CAR | GTN | ACN | TCN | TCN | AAR | AAR | YTN | MGN | 1536 |
| Ile | Gln | Asp | Tyr | Val | Ala | Gly | Gln | Val | Thr | Ser | Ser | Lys | Lys | Leu | Arg | |
| | | | 500 | | | | | 505 | | | | | 510 | | | |
| GGN | GGN | GTN | GAR | TTY | GTN | AAR | GAR | GTN | CCN | AAR | GGN | TTY | ACN | GGN | AAR | 1584 |
| Gly | Gly | Val | Glu | Phe | Val | Lys | Glu | Val | Pro | Lys | Gly | Phe | Thr | Gly | Lys | |
| | | 515 | | | | | 520 | | | | | 525 | | | | |
| ATH | GAY | ACN | MGN | AAR | ATH | AAR | GAR | ATH | YTN | ATH | AAR | GCN | CAR | AAR | GGN | 1632 |
| Ile | Asp | Thr | Arg | Lys | Ile | Lys | Glu | Ile | Leu | Ile | Lys | Ala | Gln | Lys | Gly | |
| | 530 | | | | | 535 | | | | | 540 | | | | | |
| AAR | TCN | AAR | TCN | AAR | GCN | AAR | YTN | TRR | | | | | | | | 1659 |
| Lys | Ser | Lys | Ser | Lys | Ala | Lys | Leu | | | | | | | | | |
| 545 | | | | | 550 | | | | | | | | | | | |

(SEQ ID NO:2), wherein:

A is adenine; G is guanine; C is cytosine; T is thymine; R is A or G; Y is T or C; N is A, T, C, or G; H is A, C, or T; and M is A or C;

wherein further:

(a) triplet number 553 thereof is TAA or TAG or TGA;

(b) for triplets numbered 8, 17, 26, 40, 49, 57, 63, 72, 74, 96, 114, 118, 133, 137, 143, 152, 159, 184, 189, 203, 237, 252, 255, 263, 271, 273, 276, 286, 287, 291, 294, 299, 305, 308, 318, 332, 341, 358, 373, 375, 381, 410, 437, 440, 453, 456, 457, 458, 479, 486, 511, 538, and 552, if the 3' nucleotide of a triplet is A or G, then the 5' nucleotide of said triplet is T or C, or if the 3' nucleotide of a triplet is T or C, then the 5' nucleotide of said triplet is C; and if the 5' nucleotide of a triplet is C, then the 3' nucleotide of said triplet is A, T, C, or G, or if the 5' nucleotide of a triplet is T, then the 3' nucleotide of said triplet is A or G; and (c) for triplets numbered 28, 32, 112, 130, 142, 190, 212, 217, 222, 266, 329, 336, 386, 436, 512, and 532, if the 3' nucleotide of a triplet is T or C, then the 5' nucleotide of said triplet is C; and if the 5' nucleotide of a triplet is A, then the 3' nucleotide of said triplet is A or G;

(2) A firefly luciferase gene comprising a nucleotide sequence expressed by the following:

| | | | | | | | | | | | | | | | | |
|---|---|---|---|---|---|---|---|---|---|---|---|---|---|---|---|---|
| Met | Ser | Ile | Glu | Asn | Asn | Ile | Leu | Ile | Gly | Pro | Pro | Pro | Tyr | Tyr | Pro | |
| ATG | TCA | ATA | GAG | AAT | AAC | ATT | TTG | ATA | GGA | CCA | CCT | CCG | TAC | TAT | CCT | 48 |
| 1 | | | | 5 | | | | | 10 | | | | | 15 | | |
| Leu | Glu | Glu | Gly | Thr | Ala | Gly | Glu | Gln | Leu | His | Arg | Ala | Ile | Ser | Arg | |
| TTG | GAA | GAA | GGT | ACT | GCG | GGA | GAA | CAA | TTA | CAC | AGA | GCC | ATA | TCA | CGA | 96 |
| | | | 20 | | | | | 25 | | | | | 30 | | | |
| Tyr | Ala | Ala | Val | Pro | Gly | Thr | Leu | Ala | Tyr | Thr | Asp | Val | His | Thr | Glu | |
| TAT | GCC | GCA | GTT | CCA | GGA | ACA | CTA | GCT | TAT | ACA | GAT | GTA | CAC | ACC | GAA | 144 |
| | | 35 | | | | | 40 | | | | | 45 | | | | |
| Leu | Glu | Val | Thr | Tyr | Lys | Glu | Phe | Leu | Asp | Val | Thr | Cys | Arg | Leu | Ala | |
| CTT | GAA | GTT | ACT | TAT | AAG | GAG | TTT | TTA | GAT | GTA | ACA | TGT | CGC | TTA | GCT | 192 |
| | 50 | | | | | 55 | | | | | 60 | | | | | |
| Glu | Ala | Met | Lys | Asn | Tyr | Gly | Leu | Gly | Leu | Gln | His | Thr | Ile | Ser | Val | |
| GAA | GCT | ATG | AAG | AAC | TAT | GGC | TTA | GGC | TTA | CAG | CAT | ACT | ATT | TCT | GTA | 240 |
| 65 | | | | | 70 | | | | | 75 | | | | | 80 | |
| Cys | Ser | Glu | Asn | Cys | Val | Gln | Phe | Phe | Met | Pro | Ile | Cys | Ala | Ala | Leu | |
| TGT | AGT | GAA | AAC | TGC | GTA | CAA | TTC | TTT | ATG | CCA | ATT | TGC | GCT | GCT | TTA | 288 |
| | | | | 85 | | | | | 90 | | | | | 95 | | |
| Tyr | Val | Gly | Val | Ala | Thr | Ala | Pro | Thr | Asn | Asp | Ile | Tyr | Asn | Glu | Arg | |
| TAT | GTT | GGG | GTT | GCA | ACC | GCG | CCT | ACA | AAC | GAT | ATT | TAT | AAC | GAA | CGT | 336 |
| | | | 100 | | | | | 105 | | | | | 110 | | | |
| Glu | Leu | Tyr | Asn | Ser | Leu | Ser | Ile | Ser | Gln | Por | Thr | Val | Val | Phe | Thr | |
| GAA | TTG | TAT | AAC | AGC | TTG | AGT | ATC | TCA | CAG | CCA | ACT | GTA | GTA | TTT | ACA | 384 |
| | | 115 | | | | | 120 | | | | | 125 | | | | |
| Ser | Arg | Asn | Ser | Leu | Gln | Lys | Ile | Leu | Gly | Val | Gln | Ser | Arg | Leu | Pro | |
| TCT | AGA | AAC | TCA | TTG | CAG | AAA | ATT | CTA | GGA | GTA | CAA | TCA | CGT | TTA | CCT | 432 |
| | 130 | | | | | 135 | | | | | 140 | | | | | |

-continued

| | | | | | | | | | | | | | | | | |
|---|---|---|---|---|---|---|---|---|---|---|---|---|---|---|---|---|
| Ile | Ile | Lys | Lys | Ile | Ile | Ile | Leu | Asp | Gly | Lys | Lys | Asp | Tyr | Leu | Gly | |
| ATT | ATA | AAG | AAA | ATT | ATT | ATA | CTC | GAT | GGT | AAA | AAA | GAT | TAC | TTG | GGG | 480 |
| 145 | | | | | 150 | | | | | 155 | | | | | 160 | |
| Tyr | Gln | Ser | Met | Gln | Ser | Phe | Met | Lys | Glu | His | Val | Pro | Ala | Asn | Phe | |
| TAT | CAA | TCT | ATG | CAG | TCC | TTC | ATG | AAA | GAA | CAC | GTT | CCT | GCC | AAT | TTC | 528 |
| | | | | 165 | | | | | 170 | | | | | 175 | | |
| Asn | Val | Ser | Ala | Phe | Lys | Pro | Leu | Ser | Phe | Asp | Leu | Asp | Arg | Val | Ala | |
| AAT | GTA | TCA | GCA | TTT | AAA | CCA | CTT | TCA | TTT | GAT | CTT | GAC | CGA | GTT | GCA | 576 |
| | | | 180 | | | | | 185 | | | | | 190 | | | |
| Cys | Ile | Met | Asn | Ser | Ser | Gly | Ser | Thr | Gly | Leu | Pro | Lys | Gly | Val | Pro | |
| TGT | ATT | ATG | AAC | TCT | TCA | GGT | TCT | ACG | GGA | TTA | CCA | AAA | GGT | GTA | CCA | 624 |
| | | 195 | | | | | 200 | | | | | 205 | | | | |
| Ile | Ser | His | Arg | Asn | Thr | Ile | Tyr | Arg | Phe | Ser | His | Cys | Arg | Asp | Pro | |
| ATA | TCG | CAC | AGA | AAC | ACC | ATA | TAC | AGG | TTT | TCC | CAT | TGC | AGA | GAT | CCA | 672 |
| | 210 | | | | | 215 | | | | | 220 | | | | | |
| Val | Phe | Gly | Asn | Gln | Ile | Ile | Pro | Asp | Thr | Thr | Ile | Leu | Cys | Ala | Val | |
| GTA | TTT | GGC | AAT | CAA | ATT | ATT | CGG | GAT | ACA | ACT | ATA | CTA | TGT | GCT | GTT | 720 |
| 225 | | | | | 230 | | | | | 235 | | | | | 240 | |
| Pro | Phe | His | His | Ala | Phe | Gly | Thr | Phe | Thr | Asn | Leu | Gly | Tyr | Leu | Ile | |
| CCA | TTC | CAT | CAT | GCG | TTT | GGC | ACT | TTC | ACA | AAT | TTA | GGA | TAT | TTA | ATA | 768 |
| | | | | 245 | | | | | 250 | | | | | 255 | | |
| Cys | Gly | Phe | His | Val | Val | Leu | Met | Tyr | Arg | Phe | Asn | Glu | His | Leu | Phe | |
| TGT | GGC | TTG | CAC | GTA | GTG | CTT | ATG | TAC | AGA | TTC | AAT | GAA | CAT | TTA | TTC | 816 |
| | | | 260 | | | | | 265 | | | | | 270 | | | |
| Leu | Gln | Thr | Leu | Gln | Asp | Tyr | Lys | Cys | Gln | Ser | Ala | Leu | Leu | Val | Pro | |
| TTA | CAA | ACA | CTA | CAA | GAT | TAC | AAA | TGT | CAA | AGC | GCG | TTA | CTA | GTA | CCT | 864 |
| | | 275 | | | | | 280 | | | | | 285 | | | | |
| Thr | Val | Leu | Ala | Phe | Leu | Ala | Lys | Asn | Pro | Leu | Val | Asp | Lys | Tyr | Asp | |
| ACA | GTA | CTT | GCG | TTT | CTT | GCT | AAA | AAC | CCT | TTG | GTT | GAT | AAA | TAT | GAT | 912 |
| | 290 | | | | | 295 | | | | | 300 | | | | | |
| Leu | Ser | Asn | Leu | His | Glu | Ile | Ala | Ser | Gly | Gly | Ala | Pro | Leu | Ser | Lys | |
| TTA | TCA | AAT | TTA | CAT | GAA | ATT | GCT | TCT | GGG | GGT | GCC | CCA | CTT | TCA | AAA | 960 |
| 305 | | | | | 310 | | | | | 315 | | | | | 320 | |
| Glu | Ile | Ser | Glu | Ile | Ala | Ala | Lys | Arg | Phe | Lys | Leu | Pro | Gly | Ile | Arg | |
| GAA | ATT | TCA | GAA | ATA | GCA | GCA | AAA | CGA | TTT | AAA | CTA | CCA | GGA | ATA | CGA | 1008 |
| | | | | 325 | | | | | 330 | | | | | 335 | | |
| Gln | Gly | Tyr | Gly | Leu | Thr | Glu | Thr | Thr | Cys | Ala | Ile | Val | Ile | Thr | Ala | |
| CAA | GGG | TAT | GGT | CTA | ACT | GAA | ACA | ACG | TGT | GCT | ATT | GTA | ATT | ACT | GCT | 1056 |
| | | | 340 | | | | | 345 | | | | | 350 | | | |
| Glu | Gly | Glu | Phe | Lys | Leu | Gly | Ala | Val | Gly | Lys | Val | Val | Pro | Phe | Tyr | |
| GAA | GGA | GAA | TTT | AAA | CTT | GGG | GCT | GTC | GGA | AAA | GTT | GTA | CCA | TTT | TAT | 1104 |
| | | 355 | | | | | 360 | | | | | 365 | | | | |
| Ser | Leu | Lys | Val | Leu | Asp | Leu | Asn | Thr | Gly | Lys | Lys | Leu | Gly | Pro | Asn | |
| TCC | TTA | AAA | GTT | CTT | GAT | CTT | AAT | ACA | GGA | AAA | AAA | TTG | GGG | CCA | AAC | 1152 |
| | 370 | | | | | 375 | | | | | 380 | | | | | |
| Glu | Arg | Gly | Glu | Ile | Cys | Phe | Lys | Gly | Pro | Met | Ile | Met | Lys | Gly | Tyr | |
| GAG | AGG | GGG | GAA | ATA | TGT | TTC | AAA | GGA | CCT | ATG | ATT | ATG | AAA | GGT | TAT | 1200 |
| 385 | | | | | 390 | | | | | 395 | | | | | 400 | |
| Ile | Asn | Asn | Pro | Glu | Ala | Thr | Arg | Glu | Leu | Ile | Asp | Glu | Glu | Gly | Trp | |
| ATA | AAT | AAT | CCA | GAA | GCA | ACA | CGC | GAG | TTA | ATT | GAT | GAA | GAG | GGA | TGG | 1248 |
| | | | | 405 | | | | | 410 | | | | | 415 | | |
| Ile | His | Ser | Gly | Asp | Ile | Gly | Tyr | Phr | Asp | Glu | Asp | Gly | His | Val | Tyr | |
| ATA | CAC | TCT | GGT | GAT | ATA | GGA | TAT | TTT | GAT | GAA | GAT | GGC | CAT | GTA | TAC | 1296 |
| | | | 420 | | | | | 425 | | | | | 430 | | | |
| Ile | Val | Asp | Arg | Leu | Lys | Ser | Leu | Ile | Lys | Try | Lys | Gly | Try | Gln | Val | |
| ATT | GTT | GAT | CGA | TTG | AAA | TCT | TTG | ATT | AAA | TAC | AAA | GGC | TAT | CAA | GTT | 1344 |
| | | 435 | | | | | 440 | | | | | 445 | | | | |
| Pro | Pro | Ala | Glu | Leu | Glu | Ala | Leu | Leu | Leu | Gln | His | Pro | Phe | Ile | Glu | |
| CCG | CCC | GCC | GAG | TTA | GAA | GCT | TTA | CTG | CTG | CAG | CAT | CCG | TTT | ATT | GAA | 1392 |
| | 450 | | | | | 455 | | | | | 460 | | | | | |
| Asp | Ala | Gly | Val | Ala | Gly | Val | Pro | Asp | Glu | Val | Ala | Gly | Asp | Leu | Pro | |
| GAT | GCA | GGA | GTT | GCG | GGT | GTT | CCC | GAT | GAA | GTT | GCG | GGT | GAT | CTT | CCT | 1440 |
| 465 | | | | | 470 | | | | | 475 | | | | | 480 | |

-continued

| | | | | | | | | | | | | | | | | |
|---|---|---|---|---|---|---|---|---|---|---|---|---|---|---|---|---|
| Gly | Ala | Val | Val | Val | Leu | Lys | Glu | Gly | Lys | Ser | Ile | Thr | Glu | Lys | Glu | |
| GGT | GCT | GTT | GTA | GTT | TTA | AAA | GAA | GGA | AAA | TCT | ATT | ACA | GAA | AAA | GAA | 1488 |
| | | | | 485 | | | | | 490 | | | | | 495 | | |
| Ile | Gln | Asp | Tyr | Val | Ala | Gly | Gln | Val | Thr | Ser | Ser | Lys | Lys | Leu | Arg | |
| ATC | CAA | GAT | TAC | GTG | GCA | GGC | CAA | GTA | ACT | TCT | TCG | AAA | AAG | TTA | CGA | 1536 |
| | | | 500 | | | | | 505 | | | | | 510 | | | |
| Gly | Gly | Val | Glu | Phe | Val | Lys | Glu | Val | Pro | Lys | Gly | Phe | Thr | Gly | Lys | |
| GGA | GGT | GTT | GAA | TTT | GTG | AAA | GAG | GTA | CCC | AAA | GGT | TTT | ACT | GGA | AAA | 1584 |
| | | 515 | | | | | 520 | | | | | 525 | | | | |
| Ile | Asp | Thr | Arg | Lys | Ile | Lys | Glu | Ile | Leu | Ile | Lys | Ala | Gln | Lys | Gly | |
| ATT | GAT | ACC | AGA | AAA | ATA | AAA | GAA | ATA | CTT | ATT | AAG | GCA | CAA | AAA | GGC | 1632 |
| | 530 | | | | | 535 | | | | | 540 | | | | | |
| Lys | Ser | Lys | Ser | Lys | Ala | Lys | Leu | *** | | | | | | | | |
| AAA | TCC | AAA | TCC | AAA | GCC | AAA | TTG | TAA | | | | | | | | 1659 |
| 545 | | | | | 550 | | | | | | | | | | | |

(SEQ ID NO:3).

Another preferred sequence comprises the above-indicated sequence wherein any amino acid is located at codon 409 (SEQ ID NO:4).

(3) A firefly luciferase gene comprising a nucleotide sequence expressed by the following:

| | | | | | | |
|---|---|---|---|---|---|---|
| ATCTTTTTTA | CCATCGAGTA | TAATAATTTT | CTTTATAATA | GGTAAACGTG | ATTGTACTCC | 60 |
| TAGAATTTTC | TGCAATGAGT | TTCTAGATGT | AAATACTACA | GTTGGCTGTG | AGATACTCAA | 120 |
| GCTGTTATAC | AATTCACGTT | CGTTATAAAT | ATCGTTAGTT | ACCGTCACAG | AAGTAAACTA | 180 |
| GTAAAGCCAC | CATGTCAATA | GAGAATAACA | TTTTGATAGG | ACCACCTCCG | TACTATCCTT | 240 |
| TGGAAGAAGG | TACTGCGGGA | GAACAATTAC | ACAGAGCCAT | ATCACGATAT | GCCGCAGTTC | 300 |
| CAGGAACACT | AGCTTATACA | GATGTACACA | CCGAACTTGA | AGTTACTTAT | AAGGAGTTTT | 360 |
| TAGATGTAAC | ATGTCGCTTA | GCTGAAGCTA | TGAAGAACTA | TGGCTTAGGC | TTACAGCATA | 420 |
| CTATTTCTGT | ATGTAGTGAA | AACTGCGTAC | AATTCTTTAT | GCCAATTTGC | GCTGCTTTAT | 480 |
| ATGTTGGGGT | TGCAACCGCG | CCTACAAACG | ATATTTATAA | CGAACGTGAA | TTGTATAACA | 540 |
| GCTTGAGTAT | CTCACAGCCA | ACTGTAGTAT | TTACATCTAG | AAACTCATTG | CAGAAAATTC | 600 |
| TAGGAGTACA | ATCACGTTTA | CCTATTATAA | AGAAAATTAT | TATACTCGAT | GGTAAAAAAG | 660 |
| ATTACTTGGG | GTATCAATCT | ATGCAGTCCT | TCATGAAAGA | ACACGTTCCT | GCCAATTTCA | 720 |
| ATGTATCAGC | ATTTAAACCA | CTTTCATTTG | ATCTTGACCG | AGTTGCATGT | ATTATGAACT | 780 |
| CTTCAGGTTC | TACGGGATTA | CCAAAAGGTG | TACCAATATC | GCACAGAAAC | ACCATATACA | 840 |
| GGTTTTCCCA | TTGCAGAGAT | CCAGTATTTG | GCAATCAAAT | TATTCCGGAT | ACAACTATAC | 900 |
| TATGTGCTGT | TCCATTCCAT | CATGCGTTTG | GCACTTTCAC | AAATTTAGGA | TATTTAATAT | 960 |
| GTGGCTTCCA | CGTAGTGCTT | ATGTACAGAT | TCAATGAACA | TTTATTCTTA | CAAACACTAC | 1020 |
| AAGATTACAA | ATGTCAAAGC | GCGTTACTAG | TACCTACAGT | ACTTGCGTTT | CTTGCTAAAA | 1080 |

-continued

ACCCTTTGGT TGATAAATAT GATTTATCAA ATTTACATGA AATTGCTTCT GGGGGTGCCC 1140

CACTTTCAAA AGAAATTTCA GAAATAGCAG CAAAACGATT TAAACTACCA GGAATACGAC 1200

AAGGGTATGG TCTAACTGAA ACAACGTGTG CTATTGTAAT TACTGCTGAA GGAGAATTTA 1260

AACTTGGGGC TGTCGGAAAA GTTGTACCAT TTTATTCCTT AAAAGTTCTT GATCTTAATA 1320

CAGGAAAAAA ATTGGGGCCA AACGAGAGGG GGGAAATATG TTTCAAAGGA CCTATGATTA 1380

TGAAAGGTTA TATAAATAAT CCAGAAGCAA CACGCGAGTT AATTGATGAA GAGGGATGGA 1440

TACACTCTGG TGATATAGGA TATTTTGATG AAGATGGCCA TGTATACATT GTTGATCGAT 1500

TGAAATCTTT GATTAAATAC AAAGGCTATC AAGTTCCGCC CGCCGAGTTA GAAGCTTTAC 1560

TGCTGCAGCA TCCGTTTATT GAAGATGCAG GAGTTGCGGG TGTTCCCGAT GAAGTTGCGG 1620

GTGATCTTCC TGGTGCTGTT GTAGTTTTAA AAGAAGGAAA ATCTATTACA GAAAAAGAAA 1680

TCCAAGATTA CGTGGCAGGC CAAGTAACTT CTTCGAAAAA GTTACGAGGA GGTGTTGAAT 1740

TTGTGAAAGA GGTACCCAAA GGTTTTACTG GAAAAATTGA TACCAGAAAA ATAAAAGAAA 1800

TACTTATTAA GGCACAAAAA GGCAAATCCA AATCCAAAGC CAAATTGTAA ACTAAGTGTT 1860

TGTTAATGTT GTTAAACATT TTATAAAATA CACTGTAGCT ATTTATTAGT AACCAAAATG 1920

CTTCTAACAT CAAGATGCCT ATATCTAAGA ACGTTGTATT TATATACTTT GGGGTTTTTG 1980

GTGATTATGT CAAATGTATG TGTGAAAAGG GTATACGTAG TTTAAGGGAC ATAAAAATAA 2040

ATAAAATTAA TTATTGGATT TGG 2063

(SEQ ID NO:5).

(4) A firefly enzyme luciferase having an amino acid sequence expressed by the following:

Met Ser Ile Glu Asn Asn Ile Leu Ile Gly Pro Pro Pro Tyr Tyr Pro
1 5 10 15

Leu Glu Glu Gly Thr Ala Gly Glu Gln Leu His Arg Ala Ile Ser Arg
20 25 30

Tyr Ala Ala Val Pro Gly Thr Leu Ala Tyr Thr Asp Val His Thr Glu
35 40 45

Leu Glu Val Thr Tyr Lys Glu Phe Leu Asp Val Thr Cys Arg Leu Ala
50 55 60

Glu Ala Met Lys Asn Tyr Gly Leu Gly Leu Gln His Thr Ile Ser Val
65 70 75 80

Cys Ser Glu Asn Cys Val Gln Phe Phe Met Pro Ile Cys Ala Ala Leu
85 90 95

Tyr Val Gly Val Ala Thr Ala Pro Thr Asn Asp Ile Tyr Asn Glu Arg
100 105 110

Glu Leu Tyr Asn Ser Leu Ser Ile Ser Gln Pro Thr Val Val Phe Thr
115 120 125

Ser Arg Asn Ser Leu Gln Lys Ile Leu Gly Val Gln Ser Arg Leu Pro
130 135 140

Ile Ile Lys Lys Ile Ile Ile Leu Asp Gly Lys Lys Asp Tyr Leu Gly
145 150 155 160

-continued

| | | | | | | | | | | | | | | | |
|---|---|---|---|---|---|---|---|---|---|---|---|---|---|---|---|
| Tyr | Gln | Ser | Met | Gln | Ser | Phe | Met | Lys | Glu | His | Val | Pro | Ala | Asn | Phe |
| | | | | 165 | | | | | 170 | | | | | 175 | |
| Asn | Val | Ser | Ala | Phe | Lys | Pro | Leu | Ser | Phe | Asp | Leu | Asp | Arg | Val | Ala |
| | | | 180 | | | | | 185 | | | | | 190 | | |
| Cys | Ile | Met | Asn | Ser | Ser | Gly | Ser | Thr | Gly | Leu | Pro | Lys | Gly | Val | Pro |
| | | 195 | | | | | 200 | | | | | 205 | | | |
| Ile | Ser | His | Arg | Asn | Thr | Ile | Tyr | Arg | Phe | Ser | His | Cys | Arg | Asp | Pro |
| | 210 | | | | | 215 | | | | | 220 | | | | |
| Val | Phe | Gly | Asn | Gln | Ile | Ile | Pro | Asp | Thr | Thr | Ile | Leu | Cys | Ala | Val |
| 225 | | | | | 230 | | | | | 235 | | | | | 240 |
| Pro | Phe | His | His | Ala | Phe | Gly | Thr | Phe | Thr | Asn | Leu | Gly | Tyr | Leu | Ile |
| | | | | 245 | | | | | 250 | | | | | 255 | |
| Cys | Gly | Phe | His | Val | Val | Leu | Met | Tyr | Arg | Phe | Asn | Glu | His | Leu | Phe |
| | | | 260 | | | | | 265 | | | | | 270 | | |
| Leu | Gln | Thr | Leu | Gln | Asp | Tyr | Lys | Cys | Gln | Ser | Ala | Leu | Leu | Val | Pro |
| | | 275 | | | | | 280 | | | | | 285 | | | |
| Thr | Val | Leu | Ala | Phe | Leu | Ala | Lys | Asn | Pro | Leu | Val | Asp | Lys | Tyr | Asp |
| | 290 | | | | | 295 | | | | | 300 | | | | |
| Leu | Ser | Asn | Leu | His | Glu | Ile | Ala | Ser | Gly | Gly | Ala | Pro | Leu | Ser | Lys |
| 305 | | | | | 310 | | | | | 315 | | | | | 320 |
| Glu | Ile | Ser | Glu | Ile | Ala | Ala | Lys | Arg | Phe | Lys | Leu | Pro | Gly | Ile | Arg |
| | | | | 325 | | | | | 330 | | | | | 335 | |
| Gln | Gly | Tyr | Gly | Leu | Thr | Glu | Thr | Thr | Cys | Ala | Ile | Val | Ile | Thr | Ala |
| | | | 340 | | | | | 345 | | | | | 350 | | |
| Glu | Gly | Glu | Phe | Lys | Leu | Gly | Ala | Val | Gly | Lys | Val | Val | Pro | Phe | Tyr |
| | | 355 | | | | | 360 | | | | | 365 | | | |
| Ser | Leu | Lys | Val | Leu | Asp | Leu | Asn | Thr | Gly | Lys | Lys | Leu | Gly | Pro | Asn |
| | 370 | | | | | 375 | | | | | 380 | | | | |
| Glu | Arg | Gly | Glu | Ile | Cys | Phe | Lys | Gly | Pro | Met | Ile | Met | Lys | Gly | Tyr |
| 385 | | | | | 390 | | | | | 395 | | | | | 400 |
| Ile | Asn | Asn | Pro | Glu | Ala | Thr | Arg | Glu | Leu | Ile | Asp | Glu | Glu | Gly | Trp |
| | | | | 405 | | | | | 410 | | | | | 415 | |
| Ile | His | Ser | Gly | Asp | Ile | Gly | Tyr | Phe | Asp | Glu | Asp | Gly | His | Val | Tyr |
| | | | 420 | | | | | 425 | | | | | 430 | | |
| Ile | Val | Asp | Arg | Leu | Lys | Ser | Leu | Ile | Lys | Tyr | Lys | Gly | Tyr | Gln | Val |
| | | 435 | | | | | 440 | | | | | 445 | | | |
| Pro | Pro | Ala | Glu | Leu | Glu | Ala | Leu | Leu | Leu | Gln | His | Pro | Phe | Ile | Glu |
| | 450 | | | | | 455 | | | | | 460 | | | | |
| Asp | Ala | Gly | Val | Ala | Gly | Val | Pro | Asp | Glu | Val | Ala | Gly | Asp | Leu | Pro |
| 465 | | | | | 470 | | | | | 475 | | | | | 480 |
| Gly | Ala | Val | Val | Val | Leu | Lys | Glu | Gly | Lys | Ser | Ile | Thr | Glu | Lys | Glu |
| | | | | 485 | | | | | 490 | | | | | 495 | |
| Ile | Gln | Asp | Tyr | Val | Ala | Gly | Gln | Val | Thr | Ser | Ser | Lys | Lys | Leu | Arg |
| | | | 500 | | | | | 505 | | | | | 510 | | |
| Gly | Gly | Val | Glu | Phe | Val | Lys | Glu | Val | Pro | Lys | Gly | Phe | Thr | Gly | Lys |
| | | 515 | | | | | 520 | | | | | 525 | | | |
| Ile | Asp | Thr | Arg | Lys | Ile | Lys | Glu | Ile | Leu | Ile | Lys | Ala | Gln | Lys | Gly |
| | 530 | | | | | 535 | | | | | 540 | | | | |
| Lys | Ser | Lys | Ser | Lys | Ala | Lys | Leu | (SEQ ID NO:6). | | | | | | | |
| 545 | | | | | 550 | | | | | | | | | | |

(5) A recombinant vector comprising DNA whose nucleotide sequence is expressed by SEQ ID NO:1 set forth in item (1).

(6) A recombinant vector according to item 5, having a gene having a nucleotide sequence expressed by SEQ ID NO:3 set forth in item (2),inserted into a plasmid vector.

(7) A bacterium comprising a recombinant vector containing a nucleotide sequence expressed by the SEQ ID NO:1 set forth in item (1).

(8) A process for producing an enzyme comprising an amino acid sequence expressed by the SEQ ID NO:6 set forth in item (4),which process comprises cultivating a bacterium modified by a recombinant vector containing DNA having a nucleotide sequence expressed by the SEQ ID NO:1 set forth in item (1).

BRIEF DESCRIPTION OF THE DRAWINGS

FIG. 1 shows a consensual amino acid sequence and PCR primer of an enzyme related to luciferase. Symbols for nucleotides are the same as those used for item (1) above, with the addition that W is T or A and S is G or C.

DETAILED DESCRIPTION OF PREFERRED EMBODIMENTS

The enzyme gene of the present invention is characterized by containing a nucleotide chain having a sequence length of 1,659, and SEQ ID NO:1.

The preferred sequence is SEQ ID NO:3.

The gene coding an enzyme having nucleotide SEQ ID NO:5 is DNA having a sequence length of 2,063 and it can be concretely shown.

The kind of the sequence is cDNA and it is isolated from a Northern American firefly (Photuris). The sequence is characterized by coding a protein of a molecular weight of 61,000, consisting of 552 amino acids of from nucleotide No. 192 to No. 1,847.

As to the enzyme gene of the present invention, luciferase having the photogenic activity of firefly luciferin is coded.

The enzyme of the present invention is a protein having the amino acid sequence of SEQ ID NO;6, anticipated from SEQ ID NO:1, SEQ ID NO:3, and SEQ ID NO:5. The protein consists of 552 amino acids and has a molecular weight of 61,000, and has a photogenic activity as luciferase of Northern American firefly (Photuris).

The recombinant vector of the present invention contains a DNA whose nucleotide sequence is expressed by SEQ ID NO:1. Namely, the recombinant vector of the present invention includes DNA having a nucleotide sequence expressed by SEQ ID NO:3 and a functional equivalent thereto. The "functional equivalent" refers to a DNA fragment usable according to an essentially same method in order to obtain the essentially same results, in the production of the luciferase of Northern American firefly (Photuris) by means of a suitable host.

Namely, the recombinant vector refers to a DNA fragment capable of coding a protein having the same amino acid sequence even when the nucleotide sequence is different, and a DNA fragment capable of coding a protein having a luminescent activity as luciferase although there is a certain difference in the amino acid sequence accompanying a certain difference in the nucleotide sequence. Concretely, the vector exhibits a nucleotide sequence of SEQ ID NO:1 or a nucleotide sequence having a certain variation introduced thereinto.

For example, it refers to a recombinant vector having a DNA fragment containing the nucleotide sequence inserted into a plasmid vector. As such, vector pUC (C. Yanisch-Perron, J. Vieira & J. Messing, *Gene,* 33, 110–115 (1985), pIN III (Y. Masui, J. Coleman and M. Inouye, *Experimental Manipulation of Gene Expression* (ed. M. Inouye) p15, Academic Press (1983), etc. are usable.

Figure 2:
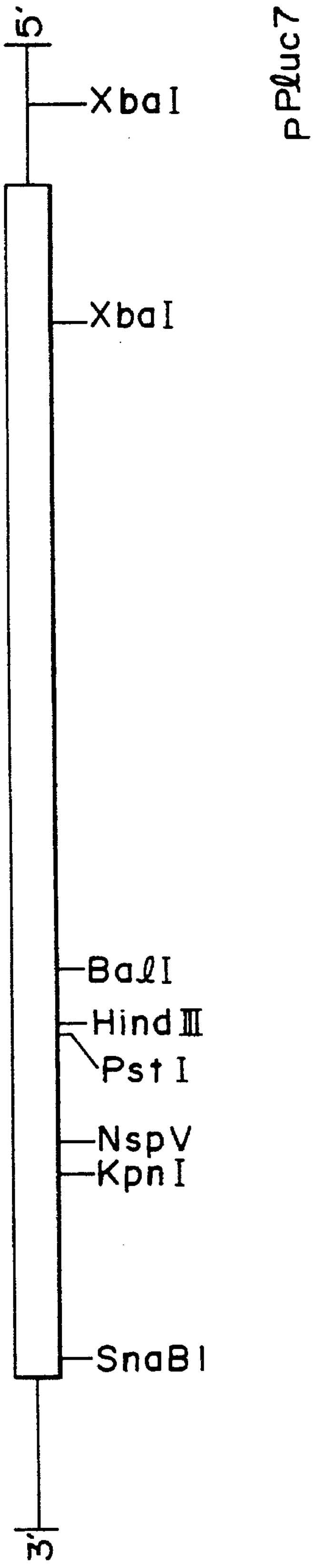
FIG. 2 shows the restriction enzyme map of the enzyme gene of the present invention. The box refers to the translated region and solid line refers to the non-translated region.
Figure 3:
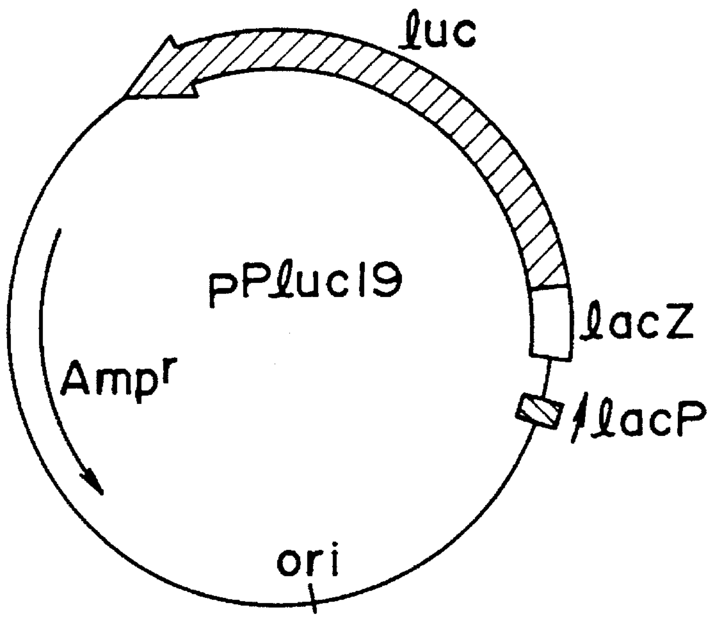
FIG. 3 shows a schematic view of the recombinant vector (expression vector pPFL 19) of the present invention containing Photuris firefly luciferase cDNA directed to the present invention.

FIG. 3 illustrates the recombinant vector (expression vector). Namely, pPFL19 isolated from cDNA library has luc gene inserted so that the translated frame of protein can accord with the lac Z gene under the rule of the lac promoter, whereby a fusion protein of β-galactosidase and luciferase can be expressed. In order to direct the substance to be constructed, ampicillin-resistant gene ($Amp^r$) and the cut site of the restriction enzyme are shown.

The bacterium of the present invention contains a recombinant vector DNA containing the nucleotide sequence expressed by SEQ ID NO:1. The characteristic of the bacterium of the present invention is to produce Photuris firefly luciferase.

The preparation of the enzyme of the present invention consists in cultivating a bacterium modified by a recombinant vector (expression vector) containing DNA expressed by nucleotide SEQ ID NO:1 to produce a protein containing an amino acid sequence expressed by SEQ ID NO:6.

As the bacterium, *Escherichia coli* is used and as the medium, LB, YT medium or the like is used.

The procedure of isolation of gene and its identification important in the present invention will be described by way of Examples.

(Example)

Example 1

(Isolation of Photuris firefly luciferase cDNA and determination of its nucleotide sequence)

Amino acid sequences of *Photinus pyralis* luciferase, *Luciola cruciata* luciferase, *Pyrophorus plagiophthalamus* luciferase and Petroselinum Crispum 4-coumerate: CoA ligase were compared. As shown in FIG. 1, oligonucleotide·primers LUC-1 (SEQ ID NO:7) and LUC-2 (SEQ ID NO:8) corresponding to the amino acid sequences within the consensual region thereof were synthesized by means of DNA synthesizer (made by ABI Co., Ltd. ) and purified by means of OPC cartridge (made by ABI Co., Ltd.).

cDNA was prepared from phage of 400,000 independent clones isolated from a cDNA library originated from the luminous organ of Photuris firefly made by Strategene Co., Ltd. according to plate lysate method (Sambrook, J., T. Maniatis and E. F. Fritsch (1989), *Molecular cloning: a laboratory manual,* 2nd ed., Cold Spring Harbor Laboratory, Cold Spring Harbor, N.Y.).

Making the cDNA a template, employing the above LUC-1 (SEQ ID NO:7) and LUC-2 (SEQ ID NO:8) each as a primer, and according to PCR method (Saiki, R. K., D. H. Gelfand, S. Stoffel, S. J. Scharf, R. Higuchi, G. T. Horn, K. B. Mullis and H. A. Erlich (1988), *Science* 239, 487), the amplification of luciferase cDNA was attempted. The PCR conditions were as follows: 94° C. for one minute, 50° C. for 2 minutes and 72° C. for 3 minutes. An amplified product was detected at about 700 bp. A fragment of the product was separated and cut out by means of agarose·gel electrophoresis and inserted into Hind II site of pUC13 plasmid, followed by determining its nucleotide sequence according to dideoxy method (Hattori, M. and Sakaki, Y. (1986), *Anal., Biochem.* 152 232). As a result, this sequence exhibited a high homology to *Photinus pyralis* firefly luciferase cDNA and Luciola firefly luciferase cDNA. Thus, we regarded this as Photuris firefly luciferase cDNA.

Using this cDNA fragment as a probe, the above-mentioned cDNA library was screened according to plaque hybridization method (Sambrook, J., T. Maniatis and E. F. Fritsch (1989), *Molecular cloning: a laboratory manual,* 2nd ed. Cold Spring Harbor Laboratory, Cold Spring Harbor, N.Y.). Nineteen positive clones were isolated from independent 200,000 clones. The positive clones of λ Zap II phase were converted into pBluescript SK plasmid.

Plasmid DNA was prepared according to alkali-SDS method and the size of inserted DNA was observed. As to two clones (pPFL7 and pPFL19) of about 1.9 kb having the largest size, their nucleotide sequences were determined. pPFL7 was completely determined and pPFL19 was partly determined.

As to pPFL7, 5'-non-translated region was present at 192 bp, and as to pPFL19, such a region was present at 6 bp. In the translated region, it was considered that a polypeptide having a molecular weight of 61,000 and consisting of 552 amino acids was coded by 1,656 bp.

Within 3'-non-translated region, poly A tail continued thereafter for 213 bp. At 24 bp and 28 bp upstream of poly A, AATAAA, which is a typical poly A signal, is present SEQ ID NO:5.

Further, the map of 6 nucleotide-recognition-restriction enzyme of pPFL7 accorded completely with that of pPFL7.

Example 2

(Expression of Photuris firefly luciferase cDNA inside the bacterial body of *Escherichia coli*)

As illustrated in FIG. 3, as to pPFL19 isolated from the cDNA library, luciferase gene (luc) has been favorably connected to lacZ in frame under the rule of lac promoter.

As a result, it is anticipated that pPFL19 will express a fusion protein of the peptide originated from β-galactosidase gene (lacZ) at N-terminal, with firefly luciferase gene (luc). pPFL19 was transformed into *Escherichia coli* D 1210. An overnight culture (0.25 ml) of the resulting transformed strain of pPFL19/D1210 was planted on an LB liquid (10 ml) medium containing ampicillin (25 ml), followed by incubating under shaking at 37° C. for 2 hours, adding isopropyl-β-D(-1)-thiogalactopyranoside (hereinafter abbreviated to IPTG) so as to give a final concentration of 1 mM and further incubating for 3 hours. At that time, the case of no addition of IPTG was also similarly tested.

The IPTG-derived-treated culture or the IPTG-not-derived culture, (each 1.5 ml) was subjected to centrifugal separation at 10,000 rpm, to remove the supernatant, followed by suspending the bacterial cells in 50 mM potassium phosphate·1 mM dithiothreitol buffer solution (0.5 ml), fracturing by ultrasonic wave, and subjecting to centrifugal separation at 12,000 rpm at 4° C. for 30 minutes, to make the resulting supernatant a cell extract liquid.

The firefly luciferase luminescent activity of the cell extract liquid was confirmed by naked eyes in a dark room.

The confirmation method of the luminescent activity of the firefly luciferase is shown below.

To the cell extract liquid (10 μl) was added a substrate mixed solution (100 mM glycylglycine pH 7.8/20 mM $MgSO_4$/0.4 mM luciferin) (100 μl), followed by pouring 20 mM ATP/25 mM glycylglycine (100 μl, pH 7.8) into the respective test tubes and confirming the luminescence after the pouring by naked eyes. The above operation was carried out in a dark room. It was found that pPFL19 had a luminescent activity i.e. firefly luciferase activity and the expression of luc gene was derived accompanying addition of IPTG. Thus, this gene could be identified to be firefly luciferase.

(Effectiveness of the Invention)

The enzyme gene of the present invention is a firefly luciferase gene and has been isolated from Photuris firefly for the first time. It is possible to prepare the firefly luciferase in a large quantity, using a suitable host, *Escherichia coli,* etc., according to a gene recombinant method. The luciferase protein catalyzes a luminescence reaction with a higher photon yield among organisms and chemical luminescences; hence it is useful for detecting a micro quantity substance with a very high sensitivity. Further, since firefly luciferin and firefly luciferase cannot be present in organisms other than fireflies, the background is almost absent even when they are used for diagnostics, etc.; hence the merit of high sensitivity of luminescence is not damaged.

Further, even when genes of other peptides are bonded thereto on a gene level, to express the resulting substance as a fusion protein, it has an activity; hence they are very advantageous when applied to diagnostics. The gene itself has almost no background as a reporter of gene expression; hence it can be applied to detection with a higher sensitivity as compared with β-galactosidase, β-glucuronidase, etc.

It is considered that coupled with recent advance of photodetector, firefly luciferase protein and gene will soon be applied to detection measurement of from one-dimension to two-dimension, further to three-dimension structure. Thus, it is considered that utilization thereof in a broader range will be desired.

What we claim is:

1. An isolated DNA molecule comprising the nucleotide sequence of SEQ ID NO:1, wherein the sequence is displayed in numbered triplets of capital letters, which numbers proceed sequentially from left to right and from the 5' terminus to the 3' terminus; and the sequence of capital letters represent the purine and pyrimidine bases of the nucleotide sequence, as follows:

A is adenine; G is guanine; C is cytosine; T is thymine;

R is A or G; Y is T or C; N is A, T, C, or G; H is A, C, or T; and M is A or C;

wherein further:

(a) triplet number 553 thereof is TAA or TAG or TGA;

(b) for triplets numbered 8, 17, 26, 40, 49, 57, 63, 72, 74, 96, 114, 118, 133, 137, 143, 152, 159, 184, 189, 203, 237, 252, 255, 263, 271, 273, 276, 286, 287, 291, 294, 299, 305, 308, 318, 332, 341, 358, 373, 375, 381, 410, 437, 440, 453, 456, 457, 458, 479, 486, 511, 538, and 552, if the 3' nucleotide of a triplet is A or G, then the 5' nucleotide of said triplet is T or C, or if the 3' nucleotide of a triplet is T or C, then the 5' nucleotide of said triplet is C; and if the 5' nucleotide of a triplet is C, then the 3' nucleotide of said triplet is A, T, C, or G, or if the 5' nucleotide of a triplet is T, then the 3' nucleotide of said triplet is A or G; and (c) for triplets numbered 28, 32, 112, 130, 142, 190, 212, 217, 222, 266, 329, 336, 386, 436, 512, and 532, if the 3' nucleotide of a triplet is T or C, then the 5' nucleotide of said triplet is A or C, or if the 3' nucleotide of a triplet is T or C, then the 5' nucleotide of said triplet is C; and if the 5' nucleotide of a triplet is G, then the 3' nucleotide of said triplet is A, T, C, or G, or if the 5' nucleotide of a triplet is A, then the 3' nucleotide of said triplet is A or G.

2. An isolated DNA molecule according to claim 1, wherein said DNA molecule has the nucleotide sequence of SEQ ID NO:3.

3. An isolated DNA molecule having the nucleotide sequence of SEQ ID NO:5.

4. A recombinant vector comprising the DNA molecule as set forth in claim 1.

5. The recombinant vector according to claim 4, wherein SEQ ID NO:3 is inserted into a plasmid vector.

6. A bacterium having a recombinant vector comprising the DNA molecule according to claim 1.

7. A process for producing an enzyme having the amino acid sequence of SEQ ID NO:6, comprising cultivating a bacterium according to claim 6.

8. An isolated DNA molecule comprising the nucleotide sequence of SEQ ID NO:2, wherein the sequence is displayed in numbered triplets of capital letters, which numbers proceed sequentially from left to right and from the 5' terminus to the 3' terminus; and the sequence of capital letters represent the purine and pyrimidine bases of the nucleotide sequence, as follows:

A is adenine; G is guanine; C is cytosine; T is thymine;

R is A or G; Y is T or C; N is A, T, C, or G; H is A, C, or T; and M is A or C;

wherein further:

(a) triplet number 553 thereof is TAA or TAG or TGA;

(b) for triplets numbered 8, 17, 26, 40, 49, 57, 63, 72, 74, 96, 114, 118, 133, 137, 143, 152, 159, 184, 189, 203, 237, 252, 255, 263, 271, 273, 276, 286, 287, 291, 294, 299, 305, 308, 318, 332, 341, 358, 373, 375, 381, 410, 437, 440, 453, 456, 457, 458, 479, 486, 511, 538, and 552, if the 3' nucleotide of a triplet is A or G, then 5' nucleotide of said triplet is T or C, or if the 3' nucleotide of a triplet is T or C, then the 5' nucleotide of said triplet is C; and if the 5' nucleotide of a triplet is C, then the 3' nucleotide of said triplet is A, T, C, or G, or if the 5' nucleotide of a triplet is T, then the 3' nucleotide of said triplet is A or G; and (c) for triplets numbered 28, 32, 112, 130, 142, 190, 212, 217, 222, 266, 329, 336, 386, 436, 512, and 532, if the 3' nucleotide of a triplet is T or C, then the 5' nucleotide of said triplet is C; and if the 5' nucleotide of a triplet is A, then the 3' nucleotide of said triplet is A or G.

9. A recombinant vector comprising the DNA molecule as set forth in claim 8.

10. A bacterium having a recombinant vector comprising the DNA molecule according to claim 8.

11. A process for producing an enzyme having the amino acid sequence of SEQ ID NO:6, comprising cultivating a bacterium according to claim 10.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
( A ) LENGTH: 1659 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 1..1659
( D ) OTHER INFORMATION: "Xaa"at codon 409 is either Glu or Asp; "Xaa"at codons 28, 32, 112, 130, 142, 190, 212, 217, 222, 266, 329, 336, 386, 436, 512, and 532 is either Arg, Ser or Gly ( x i ) SEQUENCE DESCRIPTION: SEQ ID NO:1:

```
ATG TCN ATH GAR AAY AAY ATH YTN ATH G-
GN CCN CCN CCN TAY TAY CCN          48
Met Ser Ile Glu Asn Asn Ile Leu Ile Gly Pro Pro Pro Tyr Tyr Pro
  1               5                  10                  15

YTN GAR GAR GGN ACN GCN GGN GAR-
CAR YTN CAY MGN GCN ATH TCN MGN          96
Leu Glu Glu Gly Thr Ala Gly Glu Gln Leu His Xaa Ala Ile Ser Xaa
            20                  25                  30

TAY GCN GCN GTN CCN GGN ACN YTN GCN-
TAY ACN GAY GTN CAY ACN GAR          144
Tyr Ala Ala Val Pro Gly Thr Leu Ala Tyr Thr Asp Val His Thr Glu
        35                  40                  45

YTN GAR GTN ACN TAY AAR GAR TTY YT-
N GAY GTN ACN TGY CGC YTN GCN          192
Leu Glu Val Thr Tyr Lys Glu Phe Leu Asp Val Thr Cys Arg Leu Ala
    50                  55                  60

GAR GCN ATG AAR AAY TAY GGN YTN GGN Y-
TN CAR CAY ACN ATH TCN GTN          240
Glu Ala Met Lys Asn Tyr Gly Leu Gly Leu Gln His Thr Ile Ser Val
 65                  70                  75                  80

TGY TCN GAR AAY TGY GTN CAR TTY T-
TY ATG CCN ATH TGY GCN GCN YTN          288
Cys Ser Glu Asn Cys Val Gln Phe Phe Met Pro Ile Cys Ala Ala Leu
                 85                  90                  95

TAY GTN GGN GTN GCN ACN GCN CCN AC-
N AAY GAY ATH TAY AAY GAR MGN          336
Tyr Val Gly Val Ala Thr Ala Pro Thr Asn Asp Ile Tyr Asn Glu Xaa
            100                 105                 110

GAR YTN TAY AAY TCN YTN TCN ATH TCN-
CAR CCN ACN GTN GTN TTY ACN          384
Glu Leu Tyr Asn Ser Leu Ser Ile Ser Gln Pro Thr Val Val Phe Thr
        115                 120                 125

TCN MGN AAY TCN YTN CAR AAR ATH YTN G-
GN GTN CAR TCN MGN YTN CCN          432
Ser Xaa Asn Ser Leu Gln Lys Ile Leu Gly Val Gln Ser Xaa Leu Pro
    130                 135                 140

ATH ATH AAR AAR ATH ATH ATH YTN GAY G-
GN AAR AAR GAY TAY YTN GGN          480
Ile Ile Lys Lys Ile Ile Ile Leu Asp Gly Lys Lys Asp Tyr Leu Gly
145                 150                 155                 160

TAY CAR TCN ATG CAR TCN TTY ATG AAR-
GAR CAY GTN CCN GCN AAY TTY          528
Tyr Gln Ser Met Gln Ser Phe Met Lys Glu His Val Pro Ala Asn Phe
                165                 170                 175

AAY GTN TCN GCN TTY AAR CCN YTN TCN T-
TY GAY YTN GAY MGN GTN GCN          576
Asn Val Ser Ala Phe Lys Pro Leu Ser Phe Asp Leu Asp Xaa Val Ala
            180                 185                 190

TGY ATH ATG AAY TCN TCN GGN TCN ACN G-
GN YTN CCN AAR GGN GTN CCN          624
Cys Ile Met Asn Ser Ser Gly Ser Thr Gly Leu Pro Lys Gly Val Pro
        195                 200                 205

ATH TCN CAY MGN AAY ACN ATH TAY MGN T-
TY TCN CAY TGY MGN GAY CCN          672
Ile Ser His Xaa Asn Thr Ile Tyr Xaa Phe Ser His Cys Xaa Asp Pro
    210                 215                 220

GTN TTY GGN AAY CAR ATH ATH CCN GAY-
ACN ACN ATH YTN TGY GCN GTN          720
Val Phe Gly Asn Gln Ile Ile Pro Asp Thr Thr Ile Leu Cys Ala Val
```

```
225                     230                     235                     240

CCN TTY CAY CAY GCN TTY GGN ACN TTY-
 ACN AAY YTN GGN TAY YTN ATH        768
Pro Phe His His Ala Phe Gly Thr Phe Thr Asn Leu Gly Tyr Leu Ile
                245                     250                     255

TGY GGN TTY CAY GTN GTN YTN ATG-
 TAY MGN TTY AAY GAR CAY YTN TTY        816
Cys Gly Phe His Val Val Leu Met Tyr Xaa Phe Asn Glu His Leu Phe
            260                     265                     270

YTN CAR ACN YTN CAR GAY TAY AAR TGY-
 CAR TCN GCN YTN YTN GTN CCN        864
Leu Gln Thr Leu Gln Asp Tyr Lys Cys Gln Ser Ala Leu Leu Val Pro
        275                     280                     285

ACN GTN YTN GCN TTY YTN GCN AAR AAY C-
CN YTN GTN GAY AAR TAY GAY        912
Thr Val Leu Ala Phe Leu Ala Lys Asn Pro Leu Val Asp Lys Tyr Asp
    290                     295                     300

YTN TCN AAY YTN CAY GAR ATH GCN TCN G-
GN GGN GCN CCN YTN TCN AAR        960
Leu Ser Asn Leu His Glu Ile Ala Ser Gly Gly Ala Pro Leu Ser Lys
305                     310                     315                     320

GAR ATH TCN GAR ATH GCN GCN AAR MGN TTY AAR YTN CCN GGN ATH MGN        1008
Glu Ile Ser Glu Ile Ala Ala Lys Xaa Phe Lys Leu Pro Gly Ile Xaa
                325                     330                     335

CAR GGN TAY GGN YTN ACN GAR ACN ACN T-
GY GCN ATH GTN ATH ACN GCN        1056
Gln Gly Tyr Gly Leu Thr Glu Thr Thr Cys Ala Ile Val Ile Thr Ala
            340                     345                     350

GAR GGN GAR TTY AAR YTN GGN GCN GTN G-
GN AAR GTN GTN CCN TTY TAY        1104
Glu Gly Glu Phe Lys Leu Gly Ala Val Gly Lys Val Val Pro Phe Tyr
        355                     360                     365

TCN YTN AAR GTN YTN GAY YTN AAY ACN G-
GN AAR AAR YTN GGN CCN AAY        1152
Ser Leu Lys Val Leu Asp Leu Asn Thr Gly Lys Lys Leu Gly Pro Asn
    370                     375                     380

GAR MGN GGN GAR ATH TGY TTY AAR GGN C-
CN ATG ATH ATG AAR GGN TAY        1200
Glu Xaa Gly Glu Ile Cys Phe Lys Gly Pro Met Ile Met Lys Gly Tyr
385                     390                     395                     400

ATH AAY AAY CCN GAR GCN ACN CGC GAN Y-
TN ATH GAY GAR GAR GGN TGG        1248
Ile Asn Asn Pro Glu Ala Thr Arg Xaa Leu Ile Asp Glu Glu Gly Trp
                405                     410                     415

ATH CAY TCN GGN GAY ATH GGN TAY T-
TY GAY GAR GAY GGN CAY GTN TAY        1296
Ile His Ser Gly Asp Ile Gly Tyr Phe Asp Glu Asp Gly His Val Tyr
            420                     425                     430

ATH GTN GAY MGN YTN AAR TCN YT-
N ATH AAR TAY AAR GGN TAY CAR GTN        1344
Ile Val Asp Xaa Leu Lys Ser Leu Ile Lys Tyr Lys Gly Tyr Gln Val
        435                     440                     445

CCN CCN GCN GAR YTN GAR GCN YTN YTN Y-
TN CAR CAY CCN TTY ATH GAR        1392
Pro Pro Ala Glu Leu Glu Ala Leu Leu Leu Gln His Pro Phe Ile Glu
    450                     455                     460

GAY GCN GGN GTN GCN GGN GTN CCN-
 GAY GAR GTN GCN GGN GAY YTN CCN        1440
Asp Ala Gly Val Ala Gly Val Pro Asp Glu Val Ala Gly Asp Leu Pro
465                     470                     475                     480

GGN GCN GTN GTN GTN YTN AAR GAR GGN AAR TCN ATH ACN GAR AAR GAR        1488
Gly Ala Val Val Val Leu Lys Glu Gly Lys Ser Ile Thr Glu Lys Glu
                485                     490                     495

ATH CAR GAY TAY GTN GCN GGN CAR GT-
N ACN TCN TCN AAR AAR YTN MGN        1536
Ile Gln Asp Tyr Val Ala Gly Gln Val Thr Ser Ser Lys Lys Leu Xaa
            500                     505                     510

GGN GGN GTN GAR TTY GTN AAR GAR GTN CCN AAR GGN TTY ACN GGN AAR        1584
```

-continued

```
Gly Gly Val Glu Phe Val Lys Glu Val Pro Lys Gly Phe Thr Gly Lys
        515                 520                 525

ATH GAY ACN MGN AAR ATH AAR GAR ATH YTN ATH AAR GCN CAR AAR GGN    1632
Ile Asp Thr Xaa Lys Ile Lys Glu Ile Leu Ile Lys Ala Gln Lys Gly
    530                 535                 540

AAR TCN AAR TCN AAR GCN AAR YTN TRR                                1659
Lys Ser Lys Ser Lys Ala Lys Leu
545                 550
```

( 2 ) INFORMATION FOR SEQ ID NO:2:

( i ) SEQUENCE CHARACTERISTICS:
( A ) LENGTH: 1659 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 1..1659
( D ) OTHER INFORMATION: for codons 28, 32, 112, 130, 142, 190, 212, 217, 222, 266, 329, 336, 386, 436, 512, and 532, if the 3'nucleotide is T or C, then the 5'nucleotide is C; and if the 5'nucleotide is A, then the 3'nucleotide is A or G ( x i ) SEQUENCE DESCRIPTION: SEQ ID NO:2:

```
ATG TCN ATH GAR AAY AAY ATH YTN ATH G-
GN CCN CCN CCN TAY TAY CCN          48
Met Ser Ile Glu Asn Asn Ile Leu Ile Gly Pro Pro Pro Tyr Tyr Pro
 1              5                  10                  15

YTN GAR GAR GGN ACN GCN GGN GAR-
CAR YTN CAY MGN GCN ATH TCN MGN          96
Leu Glu Glu Gly Thr Ala Gly Glu Gln Leu His Arg Ala Ile Ser Arg
             20                  25                  30

TAY GCN GCN GTN CCN GGN ACN YTN GCN-
TAY ACN GAY GTN CAY ACN GAR          144
Tyr Ala Ala Val Pro Gly Thr Leu Ala Tyr Thr Asp Val His Thr Glu
         35                  40                  45

YTN GAR GTN ACN TAY AAR GAR TTY YT-
N GAY GTN ACN TGY CGC YTN GCN          192
Leu Glu Val Thr Tyr Lys Glu Phe Leu Asp Val Thr Cys Arg Leu Ala
     50                  55                  60

GAR GCN ATG AAR AAY TAY GGN YTN GGN Y-
TN CAR CAY ACN ATH TCN GTN          240
Glu Ala Met Lys Asn Tyr Gly Leu Gly Leu Gln His Thr Ile Ser Val
 65                  70                  75                  80

TGY TCN GAR AAY TGY GTN CAR TTY T-
TY ATG CCN ATH TGY GCN GCN YTN          288
Cys Ser Glu Asn Cys Val Gln Phe Phe Met Pro Ile Cys Ala Ala Leu
                 85                  90                  95

TAY GTN GGN GTN GCN ACN GCN CCN AC-
N AAY GAY ATH TAY AAY GAR MGN          336
Tyr Val Gly Val Ala Thr Ala Pro Thr Asn Asp Ile Tyr Asn Glu Arg
            100                 105                 110

GAR YTN TAY AAY TCN YTN TCN ATH TCN-
CAR CCN ACN GTN GTN TTY ACN          384
Glu Leu Tyr Asn Ser Leu Ser Ile Ser Gln Pro Thr Val Val Phe Thr
        115                 120                 125

TCN MGN AAY TCN YTN CAR AAR ATH YTN G-
GN GTN CAR TCN MGN YTN CCN          432
Ser Arg Asn Ser Leu Gln Lys Ile Leu Gly Val Gln Ser Arg Leu Pro
    130                 135                 140

ATH ATH AAR AAR ATH ATH ATH YTN GAY G-
GN AAR AAR GAY TAY YTN GGN          480
Ile Ile Lys Lys Ile Ile Ile Leu Asp Gly Lys Lys Asp Tyr Leu Gly
145                 150                 155                 160

TAY CAR TCN ATG CAR TCN TTY ATG AAR-
GAR CAY GTN CCN GCN AAY TTY          528
```

-continued

```
Tyr Gln Ser Met Gln Ser Phe Met Lys Glu His Val Pro Ala Asn Phe
                165                 170                 175

AAY GTN TCN GCN TTY AAR CCN YTN TCN T-
TY GAY YTN GAY MGN GTN GCN    576
Asn Val Ser Ala Phe Lys Pro Leu Ser Phe Asp Leu Asp Arg Val Ala
            180                 185                 190

TGY ATH ATG AAY TCN TCN GGN TCN ACN G-
GN YTN CCN AAR GGN GTN CCN    624
Cys Ile Met Asn Ser Ser Gly Ser Thr Gly Leu Pro Lys Gly Val Pro
        195                 200                 205

ATH TCN CAY MGN AAY ACN ATH TAY MGN T-
TY TCN CAY TGY MGN GAY CCN    672
Ile Ser His Arg Asn Thr Ile Tyr Arg Phe Ser His Cys Arg Asp Pro
    210                 215                 220

GTN TTY GGN AAY CAR ATH ATH CCN GAY-
ACN ACN ATH YTN TGY GCN GTN    720
Val Phe Gly Asn Gln Ile Ile Pro Asp Thr Thr Ile Leu Cys Ala Val
225                 230                 235                 240

CCN TTY CAY CAY GCN TTY GGN ACN TTY-
ACN AAY YTN GGN TAY YTN ATH    768
Pro Phe His His Ala Phe Gly Thr Phe Thr Asn Leu Gly Tyr Leu Ile
                245                 250                 255

TGY GGN TTY CAY GTN GTN YTN ATG-
TAY MGN TTY AAY GAR CAY YTN TTY    816
Cys Gly Phe His Val Val Leu Met Tyr Arg Phe Asn Glu His Leu Phe
            260                 265                 270

YTN CAR ACN YTN CAR GAY TAY AAR TGY-
CAR TCN GCN YTN YTN GTN CCN    864
Leu Gln Thr Leu Gln Asp Tyr Lys Cys Gln Ser Ala Leu Leu Val Pro
        275                 280                 285

ACN GTN YTN GCN TTY YTN GCN AAR AAY C-
CN YTN GTN GAY AAR TAY GAY    912
Thr Val Leu Ala Phe Leu Ala Lys Asn Pro Leu Val Asp Lys Tyr Asp
    290                 295                 300

YTN TCN AAY YTN CAY GAR ATH GCN TCN G-
GN GGN GCN CCN YTN TCN AAR    960
Leu Ser Asn Leu His Glu Ile Ala Ser Gly Gly Ala Pro Leu Ser Lys
305                 310                 315                 320

GAR ATH TCN GAR ATH GCN GCN AAR MGN TTY AAR YTN CCN GGN ATH MGN    1008
Glu Ile Ser Glu Ile Ala Ala Lys Arg Phe Lys Leu Pro Gly Ile Arg
                325                 330                 335

CAR GGN TAY GGN YTN ACN GAR ACN ACN T-
GY GCN ATH GTN ATH ACN GCN    1056
Gln Gly Tyr Gly Leu Thr Glu Thr Thr Cys Ala Ile Val Ile Thr Ala
            340                 345                 350

GAR GGN GAR TTY AAR YTN GGN GCN GTN G-
GN AAR GTN GTN CCN TTY TAY    1104
Glu Gly Glu Phe Lys Leu Gly Ala Val Gly Lys Val Val Pro Phe Tyr
        355                 360                 365

TCN YTN AAR GTN YTN GAY YTN AAY ACN G-
GN AAR AAR YTN GGN CCN AAY    1152
Ser Leu Lys Val Leu Asp Leu Asn Thr Gly Lys Lys Leu Gly Pro Asn
    370                 375                 380

GAR MGN GGN GAR ATH TGY TTY AAR GGN C-
CN ATG ATH ATG AAR GGN TAY    1200
Glu Arg Gly Glu Ile Cys Phe Lys Gly Pro Met Ile Met Lys Gly Tyr
385                 390                 395                 400

ATH AAY AAY CCN GAR GCN ACN CGC-
GAR YTN ATH GAY GAR GAR GGN TGG    1248
Ile Asn Asn Pro Glu Ala Thr Arg Glu Leu Ile Asp Glu Glu Gly Trp
                405                 410                 415

ATH CAY TCN GGN GAY ATH GGN TAY T-
TY GAY GAR GAY GGN CAY GTN TAY    1296
Ile His Ser Gly Asp Ile Gly Tyr Phe Asp Glu Asp Gly His Val Tyr
            420                 425                 430

ATH GTN GAY MGN YTN AAR TCN YT-
N ATH AAR TAY AAR GGN TAY CAR GTN    1344
Ile Val Asp Arg Leu Lys Ser Leu Ile Lys Tyr Lys Gly Tyr Gln Val
        435                 440                 445
```

-continued

CCN CCN GCN GAR YTN GAR GCN YTN YTN Y-
TN CAR CAY CCN TTY ATH GAR 1392
Pro Pro Ala Glu Leu Glu Ala Leu Leu Leu Gln His Pro Phe Ile Glu
450 455 460

GAY GCN GGN GTN GCN GGN GTN CCN-
GAY GAR GTN GCN GGN GAY YTN CCN 1440
Asp Ala Gly Val Ala Gly Val Pro Asp Glu Val Ala Gly Asp Leu Pro
465 470 475 480

GGN GCN GTN GTN GTN YTN AAR GAR GGN AAR TCN ATH ACN GAR AAR GAR 1488
Gly Ala Val Val Val Leu Lys Glu Gly Lys Ser Ile Thr Glu Lys Glu
485 490 495

ATH CAR GAY TAY GTN GCN GGN CAR GT-
N ACN TCN TCN AAR AAR YTN MGN 1536
Ile Gln Asp Tyr Val Ala Gly Gln Val Thr Ser Ser Lys Lys Leu Arg
500 505 510

GGN GGN GTN GAR TTY GTN AAR GAR GTN CCN AAR GGN TTY ACN GGN AAR 1584
Gly Gly Val Glu Phe Val Lys Glu Val Pro Lys Gly Phe Thr Gly Lys
515 520 525

ATH GAY ACN MGN AAR ATH AAR GAR ATH YTN ATH AAR GCN CAR AAR GGN 1632
Ile Asp Thr Arg Lys Ile Lys Glu Ile Leu Ile Lys Ala Gln Lys Gly
530 535 540

AAR TCN AAR TCN AAR GCN AAR YTN TRR 1659
Lys Ser Lys Ser Lys Ala Lys Leu
545 550

( 2 ) INFORMATION FOR SEQ ID NO:3:

( i ) SEQUENCE CHARACTERISTICS:
( A ) LENGTH: 1659 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 1..1659
( D ) OTHER INFORMATION: the termination codon can comprise either TAA, TAG or TGA ( x i ) SEQUENCE DESCRIPTION: SEQ ID NO:3:

ATG TCA ATA GAG AAT AAC ATT TTG ATA GGA CCA CCT CCG TAC TAT CCT 48
Met Ser Ile Glu Asn Asn Ile Leu Ile Gly Pro Pro Pro Tyr Tyr Pro
1 5 10 15

TTG GAA GAA GGT ACT GCG GGA GAA CAA TTA CAC AGA GCC ATA TCA CGA 96
Leu Glu Glu Gly Thr Ala Gly Glu Gln Leu His Arg Ala Ile Ser Arg
20 25 30

TAT GCC GCA GTT CCA GGA ACA CTA GCT TAT ACA GAT GTA CAC ACC GAA 144
Tyr Ala Ala Val Pro Gly Thr Leu Ala Tyr Thr Asp Val His Thr Glu
35 40 45

CTT GAA GTT ACT TAT AAG GAG TTT TTA GAT GTA ACA TGT CGC TTA GCT 192
Leu Glu Val Thr Tyr Lys Glu Phe Leu Asp Val Thr Cys Arg Leu Ala
50 55 60

GAA GCT ATG AAG AAC TAT GGC TTA GGC TTA CAG CAT ACT ATT TCT GTA 240
Glu Ala Met Lys Asn Tyr Gly Leu Gly Leu Gln His Thr Ile Ser Val
65 70 75 80

TGT AGT GAA AAC TGC GTA CAA TTC TTT ATG CCA ATT TGC GCT GCT TTA 288
Cys Ser Glu Asn Cys Val Gln Phe Phe Met Pro Ile Cys Ala Ala Leu
85 90 95

TAT GTT GGG GTT GCA ACC GCG CCT ACA AAC GAT ATT TAT AAC GAA CGT 336
Tyr Val Gly Val Ala Thr Ala Pro Thr Asn Asp Ile Tyr Asn Glu Arg
100 105 110

GAA TTG TAT AAC AGC TTG AGT ATC TCA CAG CCA ACT GTA GTA TTT ACA 384
Glu Leu Tyr Asn Ser Leu Ser Ile Ser Gln Pro Thr Val Val Phe Thr
115 120 125

-continued

| | | | | | | | | | | | | | | | | |
|---|---|---|---|---|---|---|---|---|---|---|---|---|---|---|---|---|
| TCT | AGA | AAC | TCA | TTG | CAG | AAA | ATT | CTA | GGA | GTA | CAA | TCA | CGT | TTA | CCT | 432 |
| Ser | Arg | Asn | Ser | Leu | Gln | Lys | Ile | Leu | Gly | Val | Gln | Ser | Arg | Leu | Pro | |
| | 130 | | | | | 135 | | | | | 140 | | | | | |
| ATT | ATA | AAG | AAA | ATT | ATT | ATA | CTC | GAT | GGT | AAA | AAA | GAT | TAC | TTG | GGG | 480 |
| Ile | Ile | Lys | Lys | Ile | Ile | Ile | Leu | Asp | Gly | Lys | Lys | Asp | Tyr | Leu | Gly | |
| 145 | | | | | 150 | | | | | 155 | | | | | 160 | |
| TAT | CAA | TCT | ATG | CAG | TCC | TTC | ATG | AAA | GAA | CAC | GTT | CCT | GCC | AAT | TTC | 528 |
| Tyr | Gln | Ser | Met | Gln | Ser | Phe | Met | Lys | Glu | His | Val | Pro | Ala | Asn | Phe | |
| | | | | 165 | | | | | 170 | | | | | 175 | | |
| AAT | GTA | TCA | GCA | TTT | AAA | CCA | CTT | TCA | TTT | GAT | CTT | GAC | CGA | GTT | GCA | 576 |
| Asn | Val | Ser | Ala | Phe | Lys | Pro | Leu | Ser | Phe | Asp | Leu | Asp | Arg | Val | Ala | |
| | | | 180 | | | | | 185 | | | | | 190 | | | |
| TGT | ATT | ATG | AAC | TCT | TCA | GGT | TCT | ACG | GGA | TTA | CCA | AAA | GGT | GTA | CCA | 624 |
| Cys | Ile | Met | Asn | Ser | Ser | Gly | Ser | Thr | Gly | Leu | Pro | Lys | Gly | Val | Pro | |
| | | 195 | | | | | 200 | | | | | 205 | | | | |
| ATA | TCG | CAC | AGA | AAC | ACC | ATA | TAC | AGG | TTT | TCC | CAT | TGC | AGA | GAT | CCA | 672 |
| Ile | Ser | His | Arg | Asn | Thr | Ile | Tyr | Arg | Phe | Ser | His | Cys | Arg | Asp | Pro | |
| | 210 | | | | | 215 | | | | | 220 | | | | | |
| GTA | TTT | GGC | AAT | CAA | ATT | ATT | CCG | GAT | ACA | ACT | ATA | CTA | TGT | GCT | GTT | 720 |
| Val | Phe | Gly | Asn | Gln | Ile | Ile | Pro | Asp | Thr | Thr | Ile | Leu | Cys | Ala | Val | |
| 225 | | | | | 230 | | | | | 235 | | | | | 240 | |
| CCA | TTC | CAT | CAT | GCG | TTT | GGC | ACT | TTC | ACA | AAT | TTA | GGA | TAT | TTA | ATA | 768 |
| Pro | Phe | His | His | Ala | Phe | Gly | Thr | Phe | Thr | Asn | Leu | Gly | Tyr | Leu | Ile | |
| | | | | 245 | | | | | 250 | | | | | 255 | | |
| TGT | GGC | TTC | CAC | GTA | GTG | CTT | ATG | TAC | AGA | TTC | AAT | GAA | CAT | TTA | TTC | 816 |
| Cys | Gly | Phe | His | Val | Val | Leu | Met | Tyr | Arg | Phe | Asn | Glu | His | Leu | Phe | |
| | | | 260 | | | | | 265 | | | | | 270 | | | |
| TTA | CAA | ACA | CTA | CAA | GAT | TAC | AAA | TGT | CAA | AGC | GCG | TTA | CTA | GTA | CCT | 864 |
| Leu | Gln | Thr | Leu | Gln | Asp | Tyr | Lys | Cys | Gln | Ser | Ala | Leu | Leu | Val | Pro | |
| | | 275 | | | | | 280 | | | | | 285 | | | | |
| ACA | GTA | CTT | GCG | TTT | CTT | GCT | AAA | AAC | CCT | TTG | GTT | GAT | AAA | TAT | GAT | 912 |
| Thr | Val | Leu | Ala | Phe | Leu | Ala | Lys | Asn | Pro | Leu | Val | Asp | Lys | Tyr | Asp | |
| | 290 | | | | | 295 | | | | | 300 | | | | | |
| TTA | TCA | AAT | TTA | CAT | GAA | ATT | GCT | TCT | GGG | GGT | GCC | CCA | CTT | TCA | AAA | 960 |
| Leu | Ser | Asn | Leu | His | Glu | Ile | Ala | Ser | Gly | Gly | Ala | Pro | Leu | Ser | Lys | |
| 305 | | | | | 310 | | | | | 315 | | | | | 320 | |
| GAA | ATT | TCA | GAA | ATA | GCA | GCA | AAA | CGA | TTT | AAA | CTA | CCA | GGA | ATA | CGA | 1008 |
| Glu | Ile | Ser | Glu | Ile | Ala | Ala | Lys | Arg | Phe | Lys | Leu | Pro | Gly | Ile | Arg | |
| | | | | 325 | | | | | 330 | | | | | 335 | | |
| CAA | GGG | TAT | GGT | CTA | ACT | GAA | ACA | ACG | TGT | GCT | ATT | GTA | ATT | ACT | GCT | 1056 |
| Gln | Gly | Tyr | Gly | Leu | Thr | Glu | Thr | Thr | Cys | Ala | Ile | Val | Ile | Thr | Ala | |
| | | | 340 | | | | | 345 | | | | | 350 | | | |
| GAA | GGA | GAA | TTT | AAA | CTT | GGG | GCT | GTC | GGA | AAA | GTT | GTA | CCA | TTT | TAT | 1104 |
| Glu | Gly | Glu | Phe | Lys | Leu | Gly | Ala | Val | Gly | Lys | Val | Val | Pro | Phe | Tyr | |
| | | 355 | | | | | 360 | | | | | 365 | | | | |
| TCC | TTA | AAA | GTT | CTT | GAT | CTT | AAT | ACA | GGA | AAA | AAA | TTG | GGG | CCA | AAC | 1152 |
| Ser | Leu | Lys | Val | Leu | Asp | Leu | Asn | Thr | Gly | Lys | Lys | Leu | Gly | Pro | Asn | |
| | 370 | | | | | 375 | | | | | 380 | | | | | |
| GAG | AGG | GGG | GAA | ATA | TGT | TTC | AAA | GGA | CCT | ATG | ATT | ATG | AAA | GGT | TAT | 1200 |
| Glu | Arg | Gly | Glu | Ile | Cys | Phe | Lys | Gly | Pro | Met | Ile | Met | Lys | Gly | Tyr | |
| 385 | | | | | 390 | | | | | 395 | | | | | 400 | |
| ATA | AAT | AAT | CCA | GAA | GCA | ACA | CGC | GAG | TTA | ATT | GAT | GAA | GAG | GGA | TGG | 1248 |
| Ile | Asn | Asn | Pro | Glu | Ala | Thr | Arg | Glu | Leu | Ile | Asp | Glu | Glu | Gly | Trp | |
| | | | | 405 | | | | | 410 | | | | | 415 | | |
| ATA | CAC | TCT | GGT | GAT | ATA | GGA | TAT | TTT | GAT | GAA | GAT | GGC | CAT | GTA | TAC | 1296 |
| Ile | His | Ser | Gly | Asp | Ile | Gly | Tyr | Phe | Asp | Glu | Asp | Gly | His | Val | Tyr | |
| | | | 420 | | | | | 425 | | | | | 430 | | | |
| ATT | GTT | GAT | CGA | TTG | AAA | TCT | TTG | ATT | AAA | TAC | AAA | GGC | TAT | CAA | GTT | 1344 |
| Ile | Val | Asp | Arg | Leu | Lys | Ser | Leu | Ile | Lys | Tyr | Lys | Gly | Tyr | Gln | Val | |
| | | 435 | | | | | 440 | | | | | 445 | | | | |

CCG CCC GCC GAG TTA GAA GCT TTA CTG CTG CAG CAT CCG TTT ATT GAA 1392
Pro Pro Ala Glu Leu Glu Ala Leu Leu Leu Gln His Pro Phe Ile Glu
450 455 460

GAT GCA GGA GTT GCG GGT GTT CCC GAT GAA GTT GCG GGT GAT CTT CCT 1440
Asp Ala Gly Val Ala Gly Val Pro Asp Glu Val Ala Gly Asp Leu Pro
465 470 475 480

GGT GCT GTT GTA GTT TTA AAA GAA GGA AAA TCT ATT ACA GAA AAA GAA 1488
Gly Ala Val Val Val Leu Lys Glu Gly Lys Ser Ile Thr Glu Lys Glu
485 490 495

ATC CAA GAT TAC GTG GCA GGC CAA GTA ACT TCT TCG AAA AAG TTA CGA 1536
Ile Gln Asp Tyr Val Ala Gly Gln Val Thr Ser Ser Lys Lys Leu Arg
500 505 510

GGA GGT GTT GAA TTT GTG AAA GAG GTA CCC AAA GGT TTT ACT GGA AAA 1584
Gly Gly Val Glu Phe Val Lys Glu Val Pro Lys Gly Phe Thr Gly Lys
515 520 525

ATT GAT ACC AGA AAA ATA AAA GAA ATA CTT ATT AAG GCA CAA AAA GGC 1632
Ile Asp Thr Arg Lys Ile Lys Glu Ile Leu Ile Lys Ala Gln Lys Gly
530 535 540

AAA TCC AAA TCC AAA GCC AAA TTG TAA 1659
Lys Ser Lys Ser Lys Ala Lys Leu
545 550

( 2 ) INFORMATION FOR SEQ ID NO:4:

( i ) SEQUENCE CHARACTERISTICS:
( A ) LENGTH: 1659 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 1..1659
( D ) OTHER INFORMATION: the termination codon can comprise either TAA, TAG or TGA ( x i ) SEQUENCE DESCRIPTION: SEQ ID NO:4:

ATG TCA ATA GAG AAT AAC ATT TTG ATA GGA CCA CCT CCG TAC TAT CCT 48
Met Ser Ile Glu Asn Asn Ile Leu Ile Gly Pro Pro Pro Tyr Tyr Pro
1 5 10 15

TTG GAA GAA GGT ACT GCG GGA GAA CAA TTA CAC AGA GCC ATA TCA CGA 96
Leu Glu Glu Gly Thr Ala Gly Glu Gln Leu His Arg Ala Ile Ser Arg
20 25 30

TAT GCC GCA GTT CCA GGA ACA CTA GCT TAT ACA GAT GTA CAC ACC GAA 144
Tyr Ala Ala Val Pro Gly Thr Leu Ala Tyr Thr Asp Val His Thr Glu
35 40 45

CTT GAA GTT ACT TAT AAG GAG TTT TTA GAT GTA ACA TGT CGC TTA GCT 192
Leu Glu Val Thr Tyr Lys Glu Phe Leu Asp Val Thr Cys Arg Leu Ala
50 55 60

GAA GCT ATG AAG AAC TAT GGC TTA GGC TTA CAG CAT ACT ATT TCT GTA 240
Glu Ala Met Lys Asn Tyr Gly Leu Gly Leu Gln His Thr Ile Ser Val
65 70 75 80

TGT AGT GAA AAC TGC GTA CAA TTC TTT ATG CCA ATT TGC GCT GCT TTA 288
Cys Ser Glu Asn Cys Val Gln Phe Phe Met Pro Ile Cys Ala Ala Leu
85 90 95

TAT GTT GGG GTT GCA ACC GCG CCT ACA AAC GAT ATT TAT AAC GAA CGT 336
Tyr Val Gly Val Ala Thr Ala Pro Thr Asn Asp Ile Tyr Asn Glu Arg
100 105 110

GAA TTG TAT AAC AGC TTG AGT ATC TCA CAG CCA ACT GTA GTA TTT ACA 384
Glu Leu Tyr Asn Ser Leu Ser Ile Ser Gln Pro Thr Val Val Phe Thr
115 120 125

-continued

```
TCT   AGA   AAC   TCA   TTG   CAG   AAA   ATT   CTA   GGA   GTA   CAA   TCA   CGT   TTA   CCT     432
Ser   Arg   Asn   Ser   Leu   Gln   Lys   Ile   Leu   Gly   Val   Gln   Ser   Arg   Leu   Pro
      130                           135                           140

ATT   ATA   AAG   AAA   ATT   ATT   ATA   CTC   GAT   GGT   AAA   AAA   GAT   TAC   TTG   GGG     480
Ile   Ile   Lys   Lys   Ile   Ile   Ile   Leu   Asp   Gly   Lys   Lys   Asp   Tyr   Leu   Gly
145                           150                           155                           160

TAT   CAA   TCT   ATG   CAG   TCC   TTC   ATG   AAA   GAA   CAC   GTT   CCT   GCC   AAT   TTC     528
Tyr   Gln   Ser   Met   Gln   Ser   Phe   Met   Lys   Glu   His   Val   Pro   Ala   Asn   Phe
                        165                           170                           175

AAT   GTA   TCA   GCA   TTT   AAA   CCA   CTT   TCA   TTT   GAT   CTT   GAC   CGA   GTT   GCA     576
Asn   Val   Ser   Ala   Phe   Lys   Pro   Leu   Ser   Phe   Asp   Leu   Asp   Arg   Val   Ala
                  180                           185                           190

TGT   ATT   ATG   AAC   TCT   TCA   GGT   TCT   ACG   GGA   TTA   CCA   AAA   GGT   GTA   CCA     624
Cys   Ile   Met   Asn   Ser   Ser   Gly   Ser   Thr   Gly   Leu   Pro   Lys   Gly   Val   Pro
            195                           200                           205

ATA   TCG   CAC   AGA   AAC   ACC   ATA   TAC   AGG   TTT   TCC   CAT   TGC   AGA   GAT   CCA     672
Ile   Ser   His   Arg   Asn   Thr   Ile   Tyr   Arg   Phe   Ser   His   Cys   Arg   Asp   Pro
      210                           215                           220

GTA   TTT   GGC   AAT   CAA   ATT   ATT   CCG   GAT   ACA   ACT   ATA   CTA   TGT   GCT   GTT     720
Val   Phe   Gly   Asn   Gln   Ile   Ile   Pro   Asp   Thr   Thr   Ile   Leu   Cys   Ala   Val
225                           230                           235                           240

CCA   TTC   CAT   CAT   GCG   TTT   GGC   ACT   TTC   ACA   AAT   TTA   GGA   TAT   TTA   ATA     768
Pro   Phe   His   His   Ala   Phe   Gly   Thr   Phe   Thr   Asn   Leu   Gly   Tyr   Leu   Ile
                        245                           250                           255

TGT   GGC   TTC   CAC   GTA   GTG   CTT   ATG   TAC   AGA   TTC   AAT   GAA   CAT   TTA   TTC     816
Cys   Gly   Phe   His   Val   Val   Leu   Met   Tyr   Arg   Phe   Asn   Glu   His   Leu   Phe
                  260                           265                           270

TTA   CAA   ACA   CTA   CAA   GAT   TAC   AAA   TGT   CAA   AGC   GCG   TTA   CTA   GTA   CCT     864
Leu   Gln   Thr   Leu   Gln   Asp   Tyr   Lys   Cys   Gln   Ser   Ala   Leu   Leu   Val   Pro
            275                           280                           285

ACA   GTA   CTT   GCG   TTT   CTT   GCT   AAA   AAC   CCT   TTG   GTT   GAT   AAA   TAT   GAT     912
Thr   Val   Leu   Ala   Phe   Leu   Ala   Lys   Asn   Pro   Leu   Val   Asp   Lys   Tyr   Asp
      290                           295                           300

TTA   TCA   AAT   TTA   CAT   GAA   ATT   GCT   TCT   GGG   GGT   GCC   CCA   CTT   TCA   AAA     960
Leu   Ser   Asn   Leu   His   Glu   Ile   Ala   Ser   Gly   Gly   Ala   Pro   Leu   Ser   Lys
305                           310                           315                           320

GAA   ATT   TCA   GAA   ATA   GCA   GCA   AAA   CGA   TTT   AAA   CTA   CCA   GGA   ATA   CGA    1008
Glu   Ile   Ser   Glu   Ile   Ala   Ala   Lys   Arg   Phe   Lys   Leu   Pro   Gly   Ile   Arg
                        325                           330                           335

CAA   GGG   TAT   GGT   CTA   ACT   GAA   ACA   ACG   TGT   GCT   ATT   GTA   ATT   ACT   GCT    1056
Gln   Gly   Tyr   Gly   Leu   Thr   Glu   Thr   Thr   Cys   Ala   Ile   Val   Ile   Thr   Ala
                  340                           345                           350

GAA   GGA   GAA   TTT   AAA   CTT   GGG   GCT   GTC   GGA   AAA   GTT   GTA   CCA   TTT   TAT    1104
Glu   Gly   Glu   Phe   Lys   Leu   Gly   Ala   Val   Gly   Lys   Val   Val   Pro   Phe   Tyr
            355                           360                           365

TCC   TTA   AAA   GTT   CTT   GAT   CTT   AAT   ACA   GGA   AAA   AAA   TTG   GGG   CCA   AAC    1152
Ser   Leu   Lys   Val   Leu   Asp   Leu   Asn   Thr   Gly   Lys   Lys   Leu   Gly   Pro   Asn
      370                           375                           380

GAG   AGG   GGG   GAA   ATA   TGT   TTC   AAA   GGA   CCT   ATG   ATT   ATG   AAA   GGT   TAT    1200
Glu   Arg   Gly   Glu   Ile   Cys   Phe   Lys   Gly   Pro   Met   Ile   Met   Lys   Gly   Tyr
385                           390                           395                           400

ATA   AAT   AAT   CCA   GAA   GCA   ACA   CGC   NNN   TTA   ATT   GAT   GAA   GAG   GGA   TGG    1248
Ile   Asn   Asn   Pro   Glu   Ala   Thr   Arg   Xaa   Leu   Ile   Asp   Glu   Glu   Gly   Trp
                        405                           410                           415

ATA   CAC   TCT   GGT   GAT   ATA   GGA   TAT   TTT   GAT   GAA   GAT   GGC   CAT   GTA   TAC    1296
Ile   His   Ser   Gly   Asp   Ile   Gly   Tyr   Phe   Asp   Glu   Asp   Gly   His   Val   Tyr
                  420                           425                           430

ATT   GTT   GAT   CGA   TTG   AAA   TCT   TTG   ATT   AAA   TAC   AAA   GGC   TAT   CAA   GTT    1344
Ile   Val   Asp   Arg   Leu   Lys   Ser   Leu   Ile   Lys   Tyr   Lys   Gly   Tyr   Gln   Val
            435                           440                           445
```

-continued

CCG CCC GCC GAG TTA GAA GCT TTA CTG CTG CAG CAT CCG TTT ATT GAA 1392
Pro Pro Ala Glu Leu Glu Ala Leu Leu Leu Gln His Pro Phe Ile Glu
450 455 460

GAT GCA GGA GTT GCG GGT GTT CCC GAT GAA GTT GCG GGT GAT CTT CCT 1440
Asp Ala Gly Val Ala Gly Val Pro Asp Glu Val Ala Gly Asp Leu Pro
465 470 475 480

GGT GCT GTT GTA GTT TTA AAA GAA GGA AAA TCT ATT ACA GAA AAA GAA 1488
Gly Ala Val Val Val Leu Lys Glu Gly Lys Ser Ile Thr Glu Lys Glu
485 490 495

ATC CAA GAT TAC GTG GCA GGC CAA GTA ACT TCT TCG AAA AAG TTA CGA 1536
Ile Gln Asp Tyr Val Ala Gly Gln Val Thr Ser Ser Lys Lys Leu Arg
500 505 510

GGA GGT GTT GAA TTT GTG AAA GAG GTA CCC AAA GGT TTT ACT GGA AAA 1584
Gly Gly Val Glu Phe Val Lys Glu Val Pro Lys Gly Phe Thr Gly Lys
515 520 525

ATT GAT ACC AGA AAA ATA AAA GAA ATA CTT ATT AAG GCA CAA AAA GGC 1632
Ile Asp Thr Arg Lys Ile Lys Glu Ile Leu Ile Lys Ala Gln Lys Gly
530 535 540

AAA TCC AAA TCC AAA GCC AAA TTG TAA 1659
Lys Ser Lys Ser Lys Ala Lys Leu
545 550

( 2 ) INFORMATION FOR SEQ ID NO:5:

( i ) SEQUENCE CHARACTERISTICS:
( A ) LENGTH: 2063 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:5:

ATCTTTTTTA CCATCGAGTA TAATAATTTT CTTTATAATA GGTAAACGTG ATTGTACTCC 60

TAGAATTTTC TGCAATGAGT TTCTAGATGT AAATACTACA GTTGGCTGTG AGATACTCAA 120

GCTGTTATAC AATTCACGTT CGTTATAAAT ATCGTTAGTT ACCGTCACAG AAGTAAACTA 180

GTAAAGCCAC CATGTCAATA GAGAATAACA TTTTGATAGG ACCACCTCCG TACTATCCTT 240

TGGAAGAAGG TACTGCGGGA GAACAATTAC ACAGAGCCAT ATCACGATAT GCCGCAGTTC 300

CAGGAACACT AGCTTATACA GATGTACACA CCGAACTTGA AGTTACTTAT AAGGAGTTTT 360

TAGATGTAAC ATGTCGCTTA GCTGAAGCTA TGAAGAACTA TGGCTTAGGC TTACAGCATA 420

CTATTTCTGT ATGTAGTGAA AACTGCGTAC AATTCTTTAT GCCAATTTGC GCTGCTTTAT 480

ATGTTGGGGT TGCAACCGCG CCTACAAACG ATATTTATAA CGAACGTGAA TTGTATAACA 540

GCTTGAGTAT CTCACAGCCA ACTGTAGTAT TTACATCTAG AAACTCATTG CAGAAAATTC 600

TAGGAGTACA ATCACGTTTA CCTATTATAA AGAAAATTAT TATACTCGAT GGTAAAAAAG 660

ATTACTTGGG GTATCAATCT ATGCAGTCCT TCATGAAAGA ACACGTTCCT GCCAATTTCA 720

ATGTATCAGC ATTTAAACCA CTTTCATTTG ATCTTGACCG AGTTGCATGT ATTATGAACT 780

CTTCAGGTTC TACGGGATTA CCAAAAGGTG TACCAATATC GCACAGAAAC ACCATATACA 840

GGTTTTCCCA TTGCAGAGAT CCAGTATTTG GCAATCAAAT TATTCCGGAT ACAACTATAC 900

TATGTGCTGT TCCATTCCAT CATGCGTTTG GCACTTTCAC AAATTTAGGA TATTTAATAT 960

GTGGCTTCCA CGTAGTGCTT ATGTACAGAT TCAATGAACA TTTATTCTTA CAAACACTAC 1020

AAGATTACAA ATGTCAAAGC GCGTTACTAG TACCTACAGT ACTTGCGTTT CTTGCTAAAA 1080

ACCCTTTGGT TGATAAATAT GATTTATCAA ATTTACATGA AATTGCTTCT GGGGGTGCCC 1140

CACTTTCAAA AGAAATTTCA GAAATAGCAG CAAAACGATT TAAACTACCA GGAATACGAC 1200

-continued

AAGGGTATGG TCTAACTGAA ACAACGTGTG CTATTGTAAT TACTGCTGAA GGAGAATTTA 1260
AACTTGGGGC TGTCGGAAAA GTTGTACCAT TTTATTCCTT AAAAGTTCTT GATCTTAATA 1320
CAGGAAAAAA ATTGGGGCCA AACGAGAGGG GGGAAATATG TTTCAAAGGA CCTATGATTA 1380
TGAAAGGTTA TATAAATAAT CCAGAAGCAA CACGCGAGTT AATTGATGAA GAGGGATGGA 1440
TACACTCTGG TGATATAGGA TATTTTGATG AAGATGGCCA TGTATACATT GTTGATCGAT 1500
TGAAATCTTT GATTAAATAC AAAGGCTATC AAGTTCCGCC CGCCGAGTTA GAAGCTTTAC 1560
TGCTGCAGCA TCCGTTTATT GAAGATGCAG GAGTTGCGGG TGTTCCCGAT GAAGTTGCGG 1620
GTGATCTTCC TGGTGCTGTT GTAGTTTTAA AAGAAGGAAA ATCTATTACA GAAAAAGAAA 1680
TCCAAGATTA CGTGGCAGGC CAAGTAACTT CTTCGAAAAA GTTACGAGGA GGTGTTGAAT 1740
TTGTGAAAGA GGTACCCAAA GGTTTTACTG GAAAAATTGA TACCAGAAAA ATAAAAGAAA 1800
TACTTATTAA GGCACAAAAA GGCAAATCCA AATCCAAAGC CAAATTGTAA ACTAAGTGTT 1860
TGTTAATGTT GTTAAACATT TTATAAAATA CACTGTAGCT ATTTATTAGT AACCAAAATG 1920
CTTCTAACAT CAAGATGCCT ATATCTAAGA ACGTTGTATT TATATACTTT GGGGTTTTTG 1980
GTGATTATGT CAAATGTATG TGTGAAAAGG GTATACGTAG TTTAAGGGAC ATAAAAATAA 2040
ATAAAATTAA TTATTGGATT TGG 2063

(2) INFORMATION FOR SEQ ID NO:6:

(i) SEQUENCE CHARACTERISTICS:
(A) LENGTH: 552 amino acids
(B) TYPE: amino acid
(D) TOPOLOGY: linear (ii) MOLECULE TYPE: protein (xi) SEQUENCE DESCRIPTION: SEQ ID NO:6:

Met Ser Ile Glu Asn Asn Ile Leu Ile Gly Pro Pro Pro Tyr Tyr Pro
1 5 10 15

Leu Glu Glu Gly Thr Ala Gly Glu Gln Leu His Arg Ala Ile Ser Arg
20 25 30

Tyr Ala Ala Val Pro Gly Thr Leu Ala Tyr Thr Asp Val His Thr Glu
35 40 45

Leu Glu Val Thr Tyr Lys Glu Phe Leu Asp Val Thr Cys Arg Leu Ala
50 55 60

Glu Ala Met Lys Asn Tyr Gly Leu Gly Leu Gln His Thr Ile Ser Val
65 70 75 80

Cys Ser Glu Asn Cys Val Gln Phe Phe Met Pro Ile Cys Ala Ala Leu
85 90 95

Tyr Val Gly Val Ala Thr Ala Pro Thr Asn Asp Ile Tyr Asn Glu Arg
100 105 110

Glu Leu Tyr Asn Ser Leu Ser Ile Ser Gln Pro Thr Val Val Phe Thr
115 120 125

Ser Arg Asn Ser Leu Gln Lys Ile Leu Gly Val Gln Ser Arg Leu Pro
130 135 140

Ile Ile Lys Lys Ile Ile Ile Leu Asp Gly Lys Lys Asp Tyr Leu Gly
145 150 155 160

Tyr Gln Ser Met Gln Ser Phe Met Lys Glu His Val Pro Ala Asn Phe
165 170 175

Asn Val Ser Ala Phe Lys Pro Leu Ser Phe Asp Leu Asp Arg Val Ala
180 185 190

Cys Ile Met Asn Ser Ser Gly Ser Thr Gly Leu Pro Lys Gly Val Pro

-continued 195 200 205

Ile Ser His Arg Asn Thr Ile Tyr Arg Phe Ser His Cys Arg Asp Pro
210 215 220

Val Phe Gly Asn Gln Ile Ile Pro Asp Thr Thr Ile Leu Cys Ala Val
225 230 235 240

Pro Phe His His Ala Phe Gly Thr Phe Thr Asn Leu Gly Tyr Leu Ile
245 250 255

Cys Gly Phe His Val Val Leu Met Tyr Arg Phe Asn Glu His Leu Phe
260 265 270

Leu Gln Thr Leu Gln Asp Tyr Lys Cys Gln Ser Ala Leu Leu Val Pro
275 280 285

Thr Val Leu Ala Phe Leu Ala Lys Asn Pro Leu Val Asp Lys Tyr Asp
290 295 300

Leu Ser Asn Leu His Glu Ile Ala Ser Gly Gly Ala Pro Leu Ser Lys
305 310 315 320

Glu Ile Ser Glu Ile Ala Ala Lys Arg Phe Lys Leu Pro Gly Ile Arg
325 330 335

Gln Gly Tyr Gly Leu Thr Glu Thr Thr Cys Ala Ile Val Ile Thr Ala
340 345 350

Glu Gly Glu Phe Lys Leu Gly Ala Val Gly Lys Val Val Pro Phe Tyr
355 360 365

Ser Leu Lys Val Leu Asp Leu Asn Thr Gly Lys Lys Leu Gly Pro Asn
370 375 380

Glu Arg Gly Glu Ile Cys Phe Lys Gly Pro Met Ile Met Lys Gly Tyr
385 390 395 400

Ile Asn Asn Pro Glu Ala Thr Arg Glu Leu Ile Asp Glu Glu Gly Trp
405 410 415

Ile His Ser Gly Asp Ile Gly Tyr Phe Asp Glu Asp Gly His Val Tyr
420 425 430

Ile Val Asp Arg Leu Lys Ser Leu Ile Lys Tyr Lys Gly Tyr Gln Val
435 440 445

Pro Pro Ala Glu Leu Glu Ala Leu Leu Leu Gln His Pro Phe Ile Glu
450 455 460

Asp Ala Gly Val Ala Gly Val Pro Asp Glu Val Ala Gly Asp Leu Pro
465 470 475 480

Gly Ala Val Val Val Leu Lys Glu Gly Lys Ser Ile Thr Glu Lys Glu
485 490 495

Ile Gln Asp Tyr Val Ala Gly Gln Val Thr Ser Ser Lys Lys Leu Arg
500 505 510

Gly Gly Val Glu Phe Val Lys Glu Val Pro Lys Gly Phe Thr Gly Lys
515 520 525

Ile Asp Thr Arg Lys Ile Lys Glu Ile Leu Ile Lys Ala Gln Lys Gly
530 535 540

Lys Ser Lys Ser Lys Ala Lys Leu
545 550

( 2 ) INFORMATION FOR SEQ ID NO:7:

( i ) SEQUENCE CHARACTERISTICS:

( A ) LENGTH: 20 base pairs ( B ) TYPE: nucleic acid ( C ) STRANDEDNESS: single ( D ) TOPOLOGY: linear ( i i ) MOLECULE TYPE: DNA (other nucleic acid)

( x i ) SEQUENCE DESCRIPTION: SEQ ID NO:7:

-continued

```
ACNGGNYTNC CNAARGGNGT                                                  20
```

( 2 ) INFORMATION FOR SEQ ID NO:8:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (other nucleic acid)

( x i ) SEQUENCE DESCRIPTION: SEQ ID NO:8:

```
CCNACCRANG TRWSNCCNCT                                                  20
```